(12) United States Patent
Artioli et al.

(10) Patent No.: US 12,152,237 B2
(45) Date of Patent: Nov. 26, 2024

(54) FUNCTIONALIZED PLASMONIC NANOSTRUCTURES

(71) Applicants: ILLUMINA, INC., San Diego, CA (US); ILLUMINA CAMBRIDGE LIMITED, Cambridge (GB)

(72) Inventors: Gianluca Andrea Artioli, Cambridge (GB); Mathieu Lessard-Viger, San Diego, CA (US); Brian D. Mather, San Diego, CA (US); Xavier von Hatten, Cambridge (GB)

(73) Assignees: Illumina, Inc., San Diego, CA (US); Illumina Cambridge Limited, Cambridge (GB)

(*) Notice: Subject to any disclaimer, the term of this patent is extended or adjusted under 35 U.S.C. 154(b) by 214 days.

(21) Appl. No.: 17/525,553

(22) Filed: Nov. 12, 2021

(65) Prior Publication Data

US 2022/0154177 A1 May 19, 2022

Related U.S. Application Data

(60) Provisional application No. 63/114,309, filed on Nov. 16, 2020.

(51) Int. Cl.
*C12N 15/10* (2006.01)
*C08F 265/10* (2006.01)
*C08J 3/075* (2006.01)

(52) U.S. Cl.
CPC ........ *C12N 15/1068* (2013.01); *C08F 265/10* (2013.01); *C08J 3/075* (2013.01); *C08J 2333/26* (2013.01)

(58) Field of Classification Search
None
See application file for complete search history.

(56) References Cited

U.S. PATENT DOCUMENTS 7,417,096 B2 8/2008 McCormick, III et al.
RE41,005 E 11/2009 Koster et al.
9,322,823 B2 4/2016 Denomme et al.
9,506,056 B2 11/2016 Mirkin et al.
9,605,304 B2 3/2017 Lee et al.
2017/0342406 A1 11/2017 Rigatti et al.

FOREIGN PATENT DOCUMENTS

EP          2576839 B1 *  4/2013  .......... C12Q 1/6809
WO    2015100373 A2      7/2015
WO    2019060989 A1      4/2019
WO    2020005503 A1      1/2020

OTHER PUBLICATIONS

Ahern "Biochemical, Reagents Kits Offer Scientists Good Return on Investment" The Scientist, vol. 9, Issue 15, published Jul. 24, 1995. (Year: 1995).*
Manikas, Anastasios C., et al., "Bimetallic Au/Ag nanoparticle loading on PNIPAAm-VAA-CS8 thermoresponsive hydrogel surfaces using ss-DNA coupling, and their SERS efficiency", RSC Advances, vol. 5, No. 18, pp. 13507-13512, Jan. 1, 2015.
Huang, Xiaohua, et al., "Gold Nanoparticle Based Platforms for Circulating Cancer Marker Detection", Nanotheranostics, vol. 1, No. 1, pp. 80-102, Jan. 1, 2017.
Park, Hye Hun, et al., "Temperature-Responsive Hydrogel-Coated Gold Nanoshells", Gels, vol. 4, No. 2, p. 28, Mar. 26, 2018.
Wang, Chen, et al., "DNA-Based Hydrogels Loaded with Au Nanoparticles or Au Nanorods: Thermoresponsive Plasmonic Matrices for Shape-Memory, Self-Healing, Controlled Release, and Mechanical Applications", ACS Nano, vol. 13, No. 3, pp. 3424-3433, Mar. 1, 2019.

* cited by examiner

*Primary Examiner* — Nancy J Leith
*Assistant Examiner* — Jessica D Parisi
(74) *Attorney, Agent, or Firm* — Dierker & Kavanaugh, P.C.

(57) ABSTRACT

An example of a functionalized plasmonic nanostructure includes a plasmonic nanostructure core; a polymeric hydrogel attached to the plasmonic nanostructure core, the polymeric hydrogel having a thickness ranging from about 10 nm to about 200 nm; and a plurality of primers attached to side chains or arms of the polymeric hydrogel, wherein at least some of the plurality of primers are attached to the polymeric hydrogel at different distances from the plasmonic nanostructure core.

31 Claims, 4 Drawing Sheets

FUNCTIONALIZED PLASMONIC NANOSTRUCTURES

CROSS-REFERENCE TO RELATED APPLICATION

This application claims the benefit of U.S. Provisional Application Ser. No. 63/114,309, filed Nov. 16, 2020, the contents of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. In some examples, the controlled reactions alter charge, conductivity, or some other electrical property, and thus an electronic system may be used for detection. In other examples, the controlled reactions generate fluorescence, and thus an optical system may be used for detection.

SUMMARY

Plasmonic nanostructure cores are used as anchors for a polymeric hydrogel and a plurality of primers. The primers are attached to side chains or arms of the polymeric hydrogel, and at least some of the primers are positioned at different distances from the plasmonic nanostructure core. Template strands generated using the primers will also be at different distances from the plasmonic nanostructure core. When labeled nucleotides are introduced along the template strands, the optical labels attached to the labeled nucleotides will be at different distances from the plasmonic nanostructure core, depending upon the distance of the particular template strand from the plasmonic nanostructure core and the location of the particular labeled nucleotide along the particular template strand. During any given imaging event, at least some of the optical labels of incorporated labeled nucleotides will be within signal enhancing proximity of the plasmonic nanostructure core, thus enabling the plasmonic nanostructure core to enhance optical signals from these particular optical labels.

INTRODUCTION

A first aspect disclosed herein is a functionalized plasmonic nanostructure comprising a plasmonic nanostructure core; a polymeric hydrogel attached to the plasmonic nanostructure core, the polymeric hydrogel having a thickness ranging from about 10 nm to about 200 nm; a plurality of primers attached to side chains or arms of the polymeric hydrogel, wherein at least some of the plurality of primers are attached to the polymeric hydrogel at different distances from the plasmonic nanostructure core; and a mechanism to anchor the functionalized plasmonic nanostructure to a capture site of a flow cell.

In an example of the first aspect, the plasmonic nanostructure core is selected from the group consisting of a gold nanostructure, a silver nanostructure, a tin nanostructure, a rhodium nanostructure, a ruthenium nanostructure, a palladium nanostructure, an osmium nanostructure, an iridium nanostructure, a platinum nanostructure, a chromium nanostructure, a copper nanostructure, a gallium arsenide nanostructure, a doped silicon nanostructure, an aluminum nanostructure, a magnesium nanostructure, a silver and gold composite nanostructure, and combinations thereof.

In an example of the first aspect, the polymeric hydrogel includes at least one acrylamide monomer unit; and the polymeric hydrogel is a linear polymeric hydrogel or a branched polymeric hydrogel.

In an example of the first aspect, the plasmonic nanostructure core is functionalized with an alkyne, and the polymeric hydrogel includes an azide that is attached to the alkyne; or the plasmonic nanostructure core is functionalized with an azide, and the polymeric hydrogel includes a dialkyne that is attached to the azide.

In an example of the first aspect, the mechanism is a magnetic material in the plasmonic nanostructure core.

In an example of the first aspect, the mechanism is a functional agent incorporated into to the polymeric hydrogel.

In an example of the first aspect, the mechanism is a reversibly chargeable functional group attached to the polymeric hydrogel.

In an example of the first aspect, the different distances range from greater than 0 nm to about 20 nm.

It is to be understood that any features of the first aspect may be combined together in any desirable manner and/or may be combined with any of the examples disclosed herein to achieve the benefits as described in this disclosure, including, for example, enhanced fluorescence signals during imaging events in a sequencing protocol.

A second aspect disclosed herein is a kit comprising a flow cell including a plurality of capture sites; and a suspension including a liquid carrier and a plurality of functionalized plasmonic nanostructures dispersed throughout the liquid carrier, wherein each of the functionalized plasmonic nanostructures includes: a plasmonic nanostructure core; a polymeric hydrogel attached to the plasmonic nanostructure core, the polymeric hydrogel having a thickness ranging from about 10 nm to about 200 nm; a plurality of primers attached to side chains or arms of the polymeric hydrogel, wherein at least some of the plurality of primers are attached to the polymeric hydrogel at different distances from the plasmonic nanostructure core; and a mechanism to attach to the capture site of the flow cell.

In an example of the second aspect, the plasmonic nanostructure core is selected from the group consisting of a gold nanostructure, a silver nanostructure, a tin nanostructure, a rhodium nanostructure, a ruthenium nanostructure, a palladium nanostructure, an osmium nanostructure, an iridium nanostructure, a platinum nanostructure, a chromium nanostructure, a copper nanostructure, a gallium arsenide nanostructure, a doped silicon nanostructure, an aluminum nanostructure, a magnesium nanostructure, a silver and gold composite nanostructure, and combinations thereof.

In an example of the second aspect, the polymeric hydrogel includes at least one acrylamide monomer unit; and the polymeric hydrogel is a linear polymeric hydrogel or a branched polymeric hydrogel. In an example of the second aspect, each of the plurality of capture sites is magnetic; and the mechanism is a magnetic material included in the plasmonic nanostructure core.

In an example of the second aspect, each of the plurality of capture sites includes a chemical capture agent; and the mechanism is a functional agent incorporated the polymeric hydrogel.

In an example of the second aspect, each of the plurality of capture sites includes an electrostatic capture agent; and the mechanism is a reversibly chargeable functional group attached to the polymeric hydrogel.

In an example of the second aspect, the different distances range from greater than 0 nm to about 20 nm.

In an example of the second aspect, the substrate includes depressions separated by interstitial regions; and at least one of the plurality of capture sites is positioned in each of the depressions.

In an example of the second aspect, the substrate includes posts separated by interstitial regions; and at least one of the plurality of capture sites is positioned over each of the posts.

In an example of the second aspect, the substrate has a substantially flat surface; and the plurality of capture sites are positioned in a pattern across the substantially flat surface.

It is to be understood that any features of the second aspect may be combined together in any desirable manner. Moreover, it is to be understood that any combination of features of the first aspect and/or of the second aspect may be used together, and/or may be combined with any of the examples disclosed herein to achieve the benefits as described in this disclosure, including, for example, enhanced fluorescence signals during imaging events in a sequencing protocol.

A third aspect disclosed herein is a flow cell comprising a substrate including a plurality of capture sites; and functionalized plasmonic nanostructures anchored to at least some of the plurality of capture sites, each functionalized plasmonic nanostructure including: a plasmonic nanostructure core; a polymeric hydrogel attached to the plasmonic nanostructure core, the polymeric hydrogel having a thickness ranging from about 10 nm to about 200 nm; a plurality of primers attached to side chains or arms of the polymeric hydrogel, wherein at least some of the plurality of primers are attached to the polymeric hydrogel at different distances from the plasmonic nanostructure core; and a mechanism anchoring the functionalized plasmonic nanostructure to the capture site.

In an example of the third aspect, each of the plurality of capture sites is magnetic; and the mechanism is a magnetic material included in the plasmonic nanostructure core.

In an example of the third aspect, each of the plurality of capture sites includes a chemical capture agent; and the mechanism is a functional agent incorporated the polymeric hydrogel.

In an example of the third aspect, the different distances range from greater than 0 nm to about 20 nm.

In an example of the third aspect, the substrate includes depressions separated by interstitial regions; and at least one of the plurality of capture sites is positioned in each of the depressions.

In an example of the third aspect, the substrate includes posts separated by interstitial regions; and at least one of the plurality of capture sites is positioned over each of the posts.

In an example of the third aspect, the substrate has a substantially flat surface; and the plurality of capture sites is positioned in a pattern across the substantially flat surface.

It is to be understood that any features of the third aspect may be combined together in any desirable manner. Moreover, it is to be understood that any combination of features of the first aspect and/or of the second aspect and/or of the third aspect may be used together, and/or may be combined with any of the examples disclosed herein to achieve the benefits as described in this disclosure, including, for example, enhanced fluorescence signals during imaging events in a sequencing protocol.

A fourth aspect disclosed herein is a method comprising i) preparing a plurality of functionalized plasmonic nanostructures, wherein each of the functionalized plasmonic nanostructures includes: a plasmonic nanostructure core; a polymeric hydrogel attached to the plasmonic nanostructure core, the polymeric hydrogel having a thickness ranging from about 10 nm to about 200 nm; a plurality of primers attached to side chains of the polymeric hydrogel, wherein at least some of the plurality of primers are attached to the polymeric hydrogel at different distances from the plasmonic nanostructure core; and a mechanism to attach to a capture site of a flow cell; and ii) dispersing the functionalized plasmonic nanostructures throughout a liquid carrier.

In an example of the fourth aspect, preparing the functionalized plasmonic nanostructures involves copolymerizing monomers to form the polymeric hydrogel; grafting the primers to the polymeric hydrogel to generate a pre-grafted polymeric hydrogel; and coating the pre-grafted polymeric hydrogel on the plasmonic nanostructure core. In an example, the fourth aspect further comprises incorporating the mechanism after the polymeric hydrogel is formed.

In an example of the fourth aspect, preparing the functionalized plasmonic nanostructures involves copolymerizing a first monomer and a second monomer in the presence of the plasmonic nanostructure core to form the polymeric hydrogel, the first monomer having a first functional group to attach to the primer and the second monomer having a second functional group to attach to an anchoring surface group on the plasmonic nanostructure core; quenching polymerization when the thickness is achieved; and grafting the primers to the polymeric hydrogel. In an example, the fourth aspect further comprises incorporating the mechanism after the polymeric hydrogel is formed.

It is to be understood that any features of the fourth aspect may be combined together in any desirable manner. Moreover, it is to be understood that any combination of features of the first aspect and/or of the second aspect and/or of the third aspect and/or of the fourth aspect may be used together, and/or may be combined with any of the examples disclosed herein to achieve the benefits as described in this disclosure, including, for example, enhanced fluorescence signals during imaging events in a sequencing protocol.

A fifth aspect disclosed herein is a method comprising i) introducing a template nucleic acid strand to a plasmonic enhancing suspension, the plasmonic enhancing suspension including: a liquid carrier; and a plurality of functionalized plasmonic nanostructures dispersed throughout the liquid carrier, wherein each of the functionalized plasmonic nanostructures includes: a plasmonic nanostructure core; a polymeric hydrogel attached to the plasmonic nanostructure core, the polymeric hydrogel having a thickness ranging from about 10 nm to about 200 nm; a plurality of primers attached to side chains or arms of the polymeric hydrogel, wherein at least some of the plurality of primers are attached to the polymeric hydrogel at different distances from the plasmonic nanostructure core; and a mechanism to attach to a capture site of a flow cell; ii) initiating amplification of the template nucleic acid strand on the functionalized plasmonic nanostructures to form functionalized plasmonic nanostructures with a cluster of the template nucleic acid strands; and iii) introducing the functionalized plasmonic nanostructures with the cluster of the template nucleic acid strands into a flow cell including a plurality of the capture sites, whereby at least some of the functionalized plasmonic nanostructures respectively attach to at least some of the capture sites It is to be understood that any features of the fifth aspect may be combined together in any desirable manner. Moreover, it is to be understood that any combination of features of the first aspect and/or of the second aspect and/or of the third aspect and/or of the fourth aspect and/or of the fifth aspect may be used together, and/or may be combined with any of the examples disclosed herein to achieve the benefits as described in this disclosure, including, for example, enhanced fluorescence signals during imaging events in a sequencing protocol.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1A:
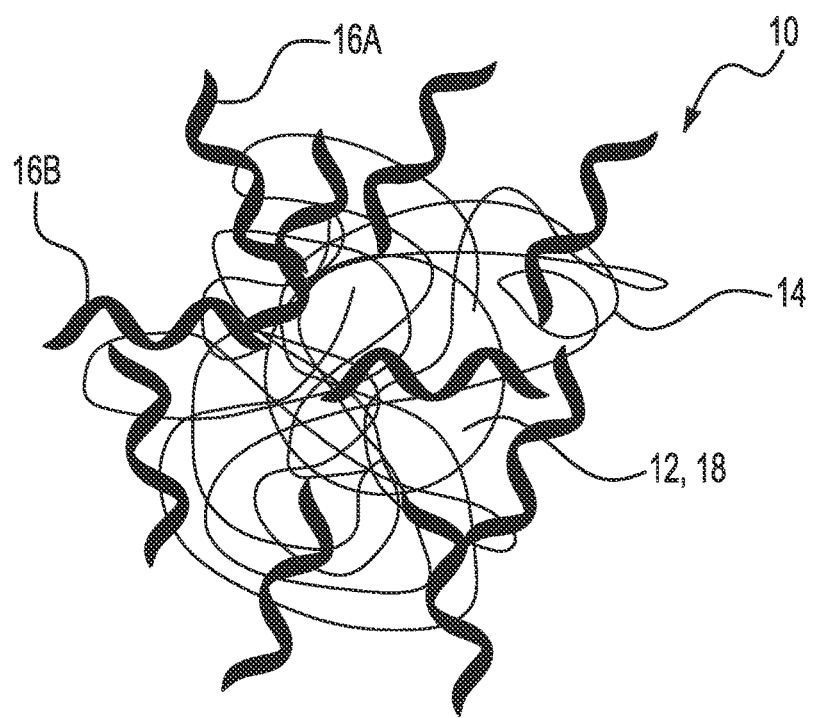
FIG. 1A is a schematic illustration of an example of a functionalized plasmonic nanostructure.

Functionalized plasmonic nanoparticles are disclosed herein. Each of the functionalized plasmonic nanoparticles includes the surface chemistry for seeding and clustering library templates as part of an off-flow cell workflow or as an on flow cell workflow. The functionalized plasmonic nanoparticles include a plasmonic nanostructure core, a polymeric hydrogel attached to the plasmonic nanostructure core, a plurality of primers attached to the polymeric hydrogel such that they are positioned at different distances from the plasmonic nanostructure core, and a mechanism to attach to a capture site of a flow cell.

Flow cells for use with the functionalized plasmonic nanoparticles are also disclosed herein. The flow cell substrate includes capture sites that can anchor the functionalized plasmonic nanoparticles at predetermined locations along the substrate. Because the polymeric hydrogel is part of the functionalized plasmonic nanoparticles, the flow cell substrate is not exposed to surface activation processes, such as silanization, to polishing processes to remove the hydrogel from interstitial regions, or to primer grafting processes. As such, the use of the functionalized plasmonic nanoparticles simplifies the flow cell substrate preparation process.

During imaging events of a sequencing protocol, the functionalized plasmonic nanoparticles anchored to the flow cell substrate can enhance optical signals. As mentioned, the primers are positioned at different distances from the plasmonic nanostructure core. Template strands generated using the primers will also be at different distances from the plasmonic nanostructure core. When labeled nucleotides are introduced along the template strands, the optical labels attached to the labeled nucleotides will be at different distances from the plasmonic nanostructure core. During any given imaging event, at least some of the optical labels of incorporated labeled nucleotides will be within signal enhancing proximity of the plasmonic nanostructure core, thus enabling the plasmonic nanostructure core to enhance optical signals from these particular optical labels. By "signal enhancing proximity," it is meant that the plasmonic nanostructure core and the optical label are separated by a distance which i) prevents quenching that can occur when the plasmonic nanostructure and the optical label are positioned too close to each other, and ii) increases plasmonic enhancement that can drop significantly at greater distances. The distance corresponding with signal enhancing proximity may range from greater than 0 nm to about 100 nm, but is dependent upon the plasmonic nanostructure (e.g., composition, shape, size) as well as the optical label. In some instances, the distance corresponding with signal enhancing proximity ranges from about 0.1 nm to about 25 nm, e.g., from about 1 nm to about 20 nm, etc. In one specific example, the distance corresponding with signal enhancing proximity ranges from about 3 nm to about 12 nm.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, adjacent, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

An "acrylamide monomer" is a monomer with the structure

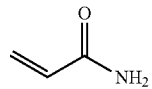

or a monomer including an acrylamide group. Examples of the monomer including an acrylamide group include azido acetamido pentyl acrylamide:

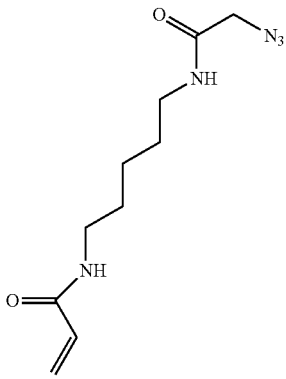 [SMILES: C=CC(=O)NCCCCCNC(=O)CN=[N+]=[N-]]

and N-isopropylacrylamide:

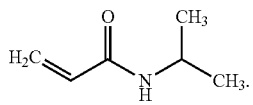

Other acrylamide monomers may be used.

An "aldehyde," as used herein, is an organic compound containing a functional group with the structure —CHO, which includes a carbonyl center (i.e., a carbon double-bonded to oxygen) with the carbon atom also bonded to hydrogen and an R group, such as an alkyl or other side chain. The general structure of an aldehyde is:

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

An "amino" functional group refers to an —NR$_a$R$_b$ group, where R$_a$ and R$_b$ are each independently selected from hydrogen (e.g.

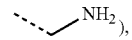

C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, the terms "anchored" and "attached" refer to the state of two things being joined, fastened, adhered, connected or bound to each other, either directly or indirectly. For example, a primer can be attached to a polymeric hydrogel by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions. Other examples of attachment include magnetic attachment or electrostatic attachment.

An "azide" or "azido" functional group refers to —N$_3$.

A "capture site", as used herein, refers to portion of a flow cell substrate having been modified, chemically, magnetically or electrostatically, that allows for anchoring of a functionalized plasmonic nanostructure. In an example, the capture site may include a chemical capture agent, a magnetic capture agent, or an electrostatic capture agent.

As used herein, "carbocycle" means a non-aromatic cyclic ring or ring system containing only carbon atoms in the ring system backbone. When the carbocycle is a ring system, two or more rings may be joined together in a fused, bridged or spiro-connected fashion. Carbocycles may have any degree of saturation, provided that at least one ring in a ring system is not aromatic. Thus, carbocycles include cycloalkyls, cycloalkenyls, and cycloalkynyls. The carbocycle group may have 3 to 20 carbon atoms. Examples of carbocycle rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to —COOH.

A "chemical capture agent" is a material, molecule or moiety that is capable of anchoring to a functional agent of a functionalized plasmonic nanostructure via a chemical mechanism. One example chemical capture agent includes a capture nucleic acid (e.g., a capture oligonucleotide) that is complementary to at least a portion of a target nucleic acid attached to a functionalized plasmonic nanostructure. Still another example chemical capture agent includes a member of a binding pair that is capable of binding to a second member of a binding pair that is attached to the functionalized plasmonic nanostructure. Example binding pairs include a NiNTA (nickel-nitrilotriacetic acid) ligand and a histidine tag, or streptavidin or avidin and biotin, etc. Yet another example of the chemical capture agent is a chemical reagent capable of forming an electrostatic interaction, a hydrogen bond, or a covalent bond with the functionalized plasmonic nanostructure. Covalent bonds may be formed, for example, through thiol-disulfide exchange, click chemistry, Diels-Alder, Michael additions, amine-aldehyde coupling, amine-acid chloride reactions, nucleophilic substitution reactions, etc. Some chemical capture agents may be light-triggered, i.e., activated to chemically bind to the chemical capture agent when exposed to light.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some examples, cycloalkyl groups can contain 3 to 8 atoms in the ring(s). A cycloalkyl group may be unsubstituted or substituted. Example cycloalkyl groups include cyclopropyl, cyclobutyl, cyclopentyl, cyclohexyl, cycloheptyl, and cyclooctyl.

As used herein, "cycloalkenyl" or "cycloalkene" means a carbocycle ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocycle ring or ring system with at least one heteroatom in ring backbone, having at least one double bond, wherein no ring in the ring system is aromatic.

As used herein, "cycloalkynyl" or "cycloalkyne" means a carbocycle ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, the term "depression" refers to a discrete concave feature defined in a substrate and having a surface opening that is at least partially surrounded by interstitial region(s) of the substrate. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc.

The term "each," when used in reference to a collection of items, is intended to identify an individual item in the collection, but does not necessarily refer to every item in the collection. Exceptions can occur if explicit disclosure or context clearly dictates otherwise.

The term "epoxy" (also referred to as a glycidyl or oxirane group) as used herein refers to

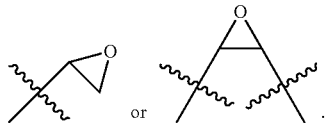

As used herein, the term "electrostatic capture agent" refers to a charged material that is capable of electrostatically anchoring a reversely charged functionalized plasmonic nanostructure. An example of an electrostatic capture agent is an electrode that can attract, when a proper voltage is applied, a reversibly chargeable functional group that is incorporated into the functionalized plasmonic nanostructure. As examples, amines or carboxylic acids can be reversibly switched between a neutral and a charged species in response to a pH change, and the charged species can be attracted to the electrode.

As used herein, the term "flow cell" is intended to mean a vessel having a flow channel where a reaction can be carried out, an inlet for delivering reagent(s) to the flow channel, and an outlet for removing reagent(s) from the flow channel. In some examples, the flow cell accommodates the detection of the reaction that occurs in the flow cell. For example, the flow cell can include one or more transparent surfaces allowing for the optical detection of arrays, optically labeled molecules, or the like.

As used herein, a "flow channel" or "channel" may be an area defined between two bonded components, which can selectively receive a liquid sample, reagents, etc. In some examples, the flow channel may be defined between two substrates, and thus may be in fluid communication with the functionalized plasmonic nanostructures anchored to each of the substrates. In other examples, the flow channel may be defined between a substrate and a lid, and thus may be in fluid communication with the functionalized plasmonic nanostructures anchored to the one substrate.

"Functionalized plasmonic nanostructures" include a plasmonic nanostructure core, a polymeric hydrogel attached to the plasmonic nanostructure core, a plurality of primers attached to side chains or arms of the polymeric hydrogel, and a mechanism to attach to a flow cell capture site. At least some of the plurality of primers of the functionalized plasmonic nanostructures are attached to the polymeric hydrogel at different distances from the plasmonic nanostructure core. The plasmonic nanostructure core may be any independent structure capable of exhibiting plasmon resonance.

A "functional agent" is a material, molecule or moiety that is capable of anchoring to a chemical capture site of a flow cell via a chemical mechanism. One example functional agent includes a target nucleic acid that is complementary to a capture nucleic acid (e.g., a capture oligonucleotide) on the flow cell. Still another example functional agent includes a member of a binding pair that is capable of binding to a second member of a binding pair that is attached to the flow cell.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocycle" means a non-aromatic cyclic ring or ring system containing at least one heteroatom in the ring backbone. Heterocycles may be joined together in a fused, bridged or spiro-connected fashion. Heterocycles may have any degree of saturation provided that at least one ring in the ring system is not aromatic. In the ring system, the heteroatom(s) may be present in either a non-aromatic or aromatic ring. The heterocycle group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

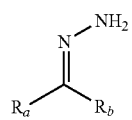

group in which $R_a$ and $R_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, "hydroxy" or "hydroxyl" refers to an —OH group.

As used herein, the term "interstitial region" refers to an area, e.g., of a substrate that separates depressions or posts or surrounds a lane. As an example, an interstitial region can separate one depression or post of an array from another depression or post of the array. As another example, an interstitial region can separate one lane of a flow cell from another lane of a flow cell. The depressions and posts and lanes that are separated from each other can be discrete, i.e., lacking physical contact with each other. In many examples, the interstitial region is continuous, whereas the depressions or posts or lanes are discrete, for example, as is the case for a plurality of depressions or lanes defined in or on an otherwise continuous surface. The separation provided by an interstitial region can be partial or full separation. Interstitial regions may have a surface material that differs from the surface material of the depressions or posts or lanes. For example, depressions and posts and lanes can have the polymeric hydrogel and primers therein or thereon, and the interstitial regions can be free of both the polymeric hydrogel and primers.

As used herein, the term "magnetic capture agent" refers to a magnetic material that is capable of magnetically anchoring a functionalized plasmonic nanostructure. Example magnetic capture agents include ferromagnetic materials and ferrimagnetic materials.

As used herein, the term "mechanism" refers to a functional agent, a magnetic material or a reversibly chargeable functional group that is incorporated into the plasmonic nanostructure core and/or the polymeric hydrogel in order to render the functionalized plasmonic nanostructures capable of anchoring to a capture site in a flow cell. The mechanism can be a material of the plasmonic nanostructure core and/or may be a functional agent that is part of or introduced to the polymeric hydrogel.

"Nitrile oxide," as used herein, means a "$R_a C \equiv N^+ O^-$" group in which $R_a$ is defined herein. Examples of preparing nitrile oxide include in situ generation from aldoximes by treatment with chloramide-T or through action of base on imidoyl chlorides [RC(Cl)=NOH] or from the reaction between hydroxylamine and an aldehyde.

"Nitrone," as used herein, means a

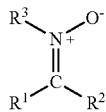

group in which $R^1$, $R^2$, and $R^3$ may be any of the $R_a$ and $R_b$ groups defined herein, except that $R^3$ is not hydrogen (H).

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA). A "labeled nucleotide" is a nucleotide that has at least an optical label attached thereto. Examples of optical labels include any dye that is capable of emitting an optical signal in response to an excitation wavelength.

The term "polymeric hydrogel" refers to a semi-rigid polymer that is permeable to liquids and gases. The polymeric hydrogel can swell when liquid (e.g., water) is taken up and that can contract when liquid is removed, e.g., by drying. While a hydrogel may absorb water, it is not water-soluble.

As used herein, the term "post" refers to a discrete convex feature defined in a substrate and having a top surface to receive a functionalized plasmonic nanostructure and a base portion that is at least partially surrounded by interstitial region(s) of the substrate. Posts can have any of a variety of shapes at the top portion including, as examples, round, elliptical, square, polygonal, star shaped (with any number of vertices), etc. The cross-section of a post taken orthogonally with the surface can be curved, square, polygonal, hyperbolic, conical, angular, etc.

As used herein, the term "primer" is defined as a single stranded nucleic acid sequence (e.g., single stranded DNA). Some primers, referred to herein as amplification primers, serve as a starting point for template amplification and cluster generation. Other primers, referred to herein as sequencing primers, serve as a starting point for DNA synthesis. The 5' terminus of the primer may be modified to allow a coupling reaction with a functional group of the polymeric hydrogel. The primer length can be any number of bases long and can include a variety of non-natural nucleotides. In an example, the sequencing primer is a short strand, ranging from 10 to 60 bases, or from 20 to 40 bases.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

Functionalized Plasmonic Nanostructures

Figure 1B:
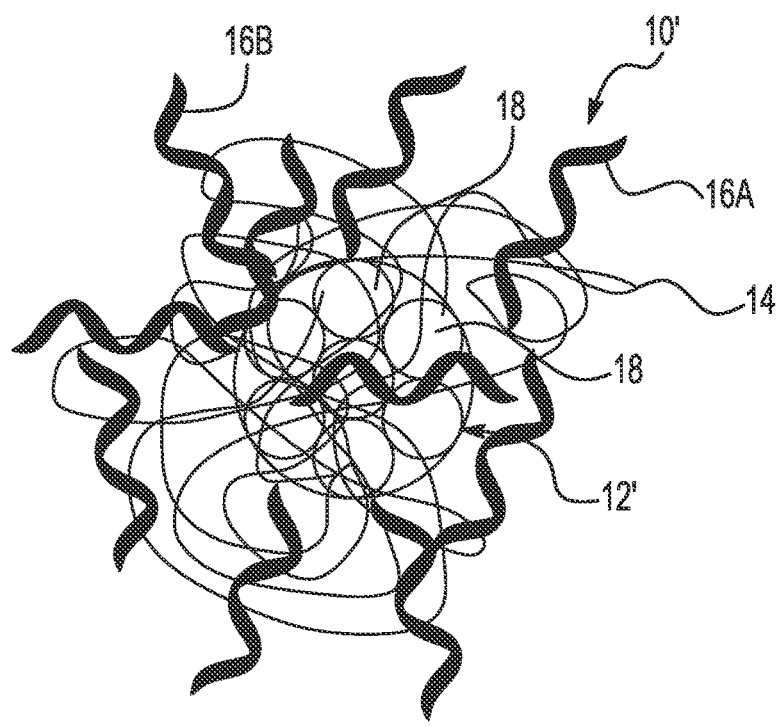
FIG. 1B is a schematic illustration of another example of a functionalized plasmonic nanostructure.

Examples of the functionalized plasmonic nanostructure 10, 10' are shown in FIG. 1A and FIG. 1B. Each of the functionalized plasmonic nanostructures 10, 10' includes a plasmonic nanostructure core 12, 12'; a polymeric hydrogel 14 attached to the plasmonic nanostructure core 12, 12', the polymeric hydrogel 14 having a thickness ranging from about 10 nm to about 200 nm; a plurality of primers 16A, 16B attached to side chains or arms of the polymeric hydrogel 14, wherein at least some of the plurality of primers 16A, 16B are attached to the polymeric hydrogel 14 at different distances from the plasmonic nanostructure core 12, 12', and a mechanism (not shown) to attach to a capture site of a flow cell.

In the example shown in FIG. 1A, the plasmonic nanostructure core 12 includes a single plasmonic nanostructure 18. In the example shown in FIG. 1B, the plasmonic nanostructure core 12' includes a plurality of plasmonic nanostructures 18 clustered together. Single plasmonic nanostructures 18 as the core 12 may be desirable when the depressions or posts are sized for single occupancy. A plurality of plasmonic nanostructures 18 as the core 12' may be desirable when the capture sites are larger than the plasmonic nanostructures 18.

The plasmonic nanostructure(s) 18 making up the core 12, 12' include any independent structure capable of exhibiting plasmon resonance. Plasmon resonance is the phenomenon where the electrons in the material surface layer are excited by photons of incident light with a certain angle of incidence, and then propagate parallel to the material surface. The surfaces of plasmonic nanostructures can strongly confine an electromagnetic field through its coupling to the propagating or localized surface plasmons. This interaction is associated with a large enhancement of the local electrical field, which in turn can enhance the excitation and emission rates and decrease the lifetimes of excited states of fluorescence emitters. This results in an amplified fluorescence signal and may also improve resistance to photobleaching.

Any material capable of plasmon resonance, referred to herein as a "plasmonic material", may be used as the plasmonic nanostructure(s) 18 (and thus the core 12, 12'). Several metals (e.g., gold, silver, tin, rhodium, ruthenium, palladium, osmium, iridium, platinum, copper, aluminum, etc.), doped semi-metals (e.g., doped silicon), direct bandgap semiconductors (e.g., gallium arsenide), and metal composites or metal alloys are capable of plasmon resonance. Metal composites or metal alloys may include and two or more of the metals listed above. As examples, a two-metal composite includes silver and gold and a three-metal composite includes silver, gold, and platinum. Some metal composites (e.g., silver and iron) or metal alloys (e.g., gold and iron) may be used that include a plasmonic metal and a magnetic metal. Such a composite or alloy is desirable when the flow cell includes a magnetic capture pad. In any of the examples set forth herein, the plasmonic nanostructure(s) 18 may be selected from the group consisting of a gold nanostructure, a silver nanostructure, a tin nanostructure, a rhodium nanostructure, a ruthenium nanostructure, a palladium nanostructure, an osmium nanostructure, an iridium nanostructure, a platinum nanostructure, a chromium nanostructure, a copper nanostructure, a gallium arsenide nanostructure, a doped silicon nanostructure, an aluminum nanostructure, a magnesium nanostructure, a silver and gold composite nanostructure, and combinations thereof.

In an example, the plasmonic nanostructure(s) 18 are spherical nanoparticles. In another example, the plasmonic nanostructure(s) 18 are non-spherical nanoparticles, such as cubes, triangular prisms, rod shaped, platelets, cage-like (e.g., non-spherical, hollow particles having a porous shell), tubes, etc. In still another example, the plasmonic nanostructure(s) are irregularly shaped nanoparticles. The morphology of the plasmonic nanostructure(s) 18 may affect the magnitude of the signal enhancement in the examples disclosed herein. For example, spherical nanoparticles, nanoplatelets, and nanocubes may magnify signal enhancement more than nanotubes.

The plasmonic nanostructure(s) 18 may each have a solid structure, a hollow structure, or a core-shell structure.

The core-shell structure has one material at the interior and another material at the exterior least partially encapsulating the interior. In some examples, two different plasmonic materials may used as the interior and exterior.

In other examples, the interior is a plasmonic material and the exterior is a non-plasmonic material. Some examples of suitable exterior materials include silica, metal oxides, such as alumina, titania, and tantalum oxides, proteins, such as bovine serum albumin, and organic polymers that are transparent to the wavelengths used during sequencing, such as poly(methyl methacrylate) (PMMA), poly(lactic acid) (PLA), and poly(methyl acrylate) (PMA). The non-plasmonic material does not interfere with the plasmonic resonance of the interior, but does increase the distance of the polymeric hydrogel 14 and the primers 16A, 16B from the core 12, 12'. This type of shell may be desirable when the incoming optical labels would otherwise be too close to the core 12, 12' that quenching would occur.

In still other examples, a magnetic material (e.g., nickel, iron, cobalt, or other ferromagnetic materials, ferrites, magnetite, or other ferromagnetic materials, etc.) may be incorporated into the interior or into the exterior of the core-shell structure. As one example, the magnetic material may be used as the interior and a plasmonic material may be used as the exterior. This example core-shell structure may be suitable for use when the flow cell substrate includes a magnetic capture agent, because the magnetic material is the mechanism for attachment to the flow cell capture site.

The dimensions of the plasmonic nanostructure(s) 18 may vary depending upon its shape. In the examples disclosed herein, the largest dimension (e.g., diameter, length, median, etc.) of the plasmonic nanostructure 18 is on the nanoscale, and thus ranges from about 1 nm to less than 1000 nm. In some examples, the nanostructure(s) 18 are nanoparticles having a diameter of greater than or equal to 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, or greater than or equal to 100 nm. The size of the plasmonic nanostructure(s) 18 may affect the magnitude of the signal enhancement in some of the examples disclosed herein. More particularly, plasmonic nanostructure(s) 18 with different sizes resonate at different wavelengths. To maximize fluorescent enhancement, the nanostructure 18 resonation wavelength may be considered. For example, modeling may be used to predict the optical properties of a nanostructure 18 of a given size and shape in order to target nanostructures 18 that will resonate at a desired wavelength. In an example, modeling for spherical nanoparticles can be performed by the Mie theory, using Maxwell's equations for light scattering.

The dimensions of the core 12 will depend upon the dimensions of the plasmonic nanostructure 18, and the dimensions of the core 12' will depend upon the dimensions of the plasmonic nanostructures 18 and the number of plasmonic nanostructures 18 in the cluster.

The functionalized plasmonic nanostructures 10, 10' also include the polymeric hydrogel 14.

In some examples, the polymeric hydrogel 14 is coated on the plasmonic nanostructure core 12, 12'. Methods for coating the polymeric hydrogel 14 on the plasmonic nanostructure core 12, 12' are described in more detail below.

Some examples of the coated polymeric hydrogel 14 may at least partially encapsulate the plasmonic nanostructure core 12, 12' without being covalently bonded thereto. For example, non-specific binding could attach the polymeric hydrogel 14 to the plasmonic nanostructure core 12, 12'.

Other examples of the coated polymeric hydrogel 14 may be covalently attached to the plasmonic nanostructure core 12, 12', and thus the plasmonic nanostructure core 12, 12' (plasmonic nanostructure(s) 18) may be functionalized with anchoring surface groups to covalently attach to the polymeric hydrogel 14. As examples, the plasmonic nanostructure core 12, 12' may be functionalized with an alkyne (e.g., dibenzocyclooctyne), and the polymeric hydrogel 14 may include an azide that can attach to the alkyne; or the plasmonic nanostructure core 12, 12' is functionalized with an azide, and the polymeric hydrogel 14 may include a dialkyne that can attached to the azide. Other covalent linkages between the coated polymeric hydrogel 14 and the plasmonic nanostructure core 12, 12' are also possible, including those obtained through nucleophilic substitution reactions (e.g., between a nucleophilic group and a nucleofuge group). Some specific example include those involving an aldehyde and a hydrazine, or an amine and an activated carboxylate (e.g., N-hydroxysuccinimide ester), or a thiol and an alkylating reagent, or a phosphoramidite and a thioether.

In still other examples, the coated the polymeric hydrogel 14 may non-covalently bind to the plasmonic nanostructure core 12, 12', and thus the plasmonic nanostructure core 12, 12' (plasmonic nanostructure(s) 18) may be functionalized to non-covalently attach to the polymeric hydrogel 14. For example, the plasmonic nanostructure core 12, 12' may be functionalized with a first member of a binding pair, which interacts with a second member of the binding pair that is attached to the hydrogel 14. In example binding pairs, the first member and the second member respectively include a NiNTA (nickel-nitrilotriacetic acid) ligand and a histidine tag, or streptavidin or avidin and biotin, or a spytag and a spycatcher, etc.

In other examples, the polymeric hydrogel 14 is polymerized from the plasmonic nanostructure core 12, 12'. In these examples, the plasmonic nanostructure core 12, 12' includes an initiator or a chain transfer agent (CTA) attached to the surface of the plasmonic nanostructure(s) 18. Methods for polymerizing the polymeric hydrogel 14 from the plasmonic nanostructure core 12, 12' are described in more detail below.

In the examples disclosed herein, the polymeric hydrogel 14 is a copolymer including at least one acrylamide monomer unit, and is a linear polymeric hydrogel or branched polymeric hydrogel.

The linear or branched polymeric hydrogel 14 may include a first recurring unit of formula (I):

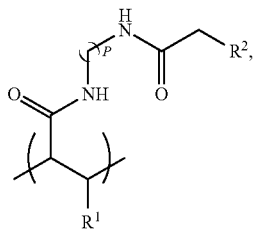

wherein:

$R^1$ is selected from the group consisting of —H, a halogen, an alkyl, an alkoxy, an alkenyl, an alkynyl, a cycloalkyl, an aryl, a heteroaryl, a heterocycle, and optionally substituted variants thereof; $R^2$ is selected from the group consisting of an azido, an optionally substituted amino, an optionally substituted alkenyl, an optionally substituted alkyne, a halogen, an optionally substituted hydrazone, an optionally substituted hydrazine, a carboxyl, a hydroxy, an optionally substituted tetrazole, an optionally substituted tetrazine, nitrile oxide, nitrone, sulfate, and thiol; each $(CH_2)_p$ can be optionally substituted; and p is an integer from 1 to 50; a second recurring unit of formula (II):

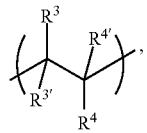

wherein: each of $R^3$, $R^{3'}$, $R^4$, $R^{4'}$ is independently selected from the group consisting of —H, $R^5$, —$OR^5$, —$C(O)OR^5$, —$C(O)R^5$, —$OC(O)R^5$, —$C(O)NR^6R^7$, and —$NR^6R^7$; $R^5$ is selected from the group consisting of —H, —OH, an alkyl, a cycloalkyl, a hydroxyalkyl, an aryl, a heteroaryl, a heterocycle, and optionally substituted variants thereof; and each of $R^6$ and $R^7$ is independently selected from the group consisting of —H and an alkyl.

In an example, $R^1$ is —H; $R^2$ is an azido; each of $R^{3'}$, $R^4$, and $R^{4'}$ is —H; $R^3$ is —$C(O)NR^6R^7$, where each of $R^6$ and $R^7$ is —H; and p is 5. This polymeric hydrogel 14 is poly(N-(5-azidoacetamidylpentyl)acrylamide-co-acrylamide, or PAZAM. In a variation of PAZAM, $R^1$ is —H; $R^2$ is an azido; each of $R^{3'}$, $R^4$, and $R^{4'}$ is —H; $R^3$ is —$C(O)NR^6R^7$, where each of $R^6$ and $R^7$ is a C1-C6 alkyl (e.g., —$CH_3$), and p is 5.

In some examples, $R^2$ of some of the recurring units of formula (I) is replaced with tetramethylethylenediamine (TeMED). TeMED is a reaction promoter that may be introduced during copolymerization. As a result of a side reaction, TeMED replaces some of the azide ($N_3$) or other $R^2$ groups. While this reaction reduces the azide (or other $R^2$ examples) content of the copolymer chains, it also introduces a branching site. The branching sites may provide a location where the copolymer chains can branch to one other.

In other examples, a third recurring unit of formula (II) may be included, with the caveat that the second and third recurring units are different. For example, in the second recurring unit each of $R^{3'}$, $R^4$, and $R^{4'}$ is —H; $R^3$ is —$C(O)NR^6R^7$, where each of $R^6$ and $R^7$ is —H, and in the third recurring unit, each of $R^{3'}$, $R^4$, and $R^{4'}$ is —H; $R^3$ is —$C(O)NR^6R^7$, where each of $R^6$ and $R^7$ is a C1-C6 alkyl.

The number of first recurring units (formula (I)) may be an integer ranging from 2 to 50,000, and the number of second recurring units (formula (II)) may be an integer ranging from 2 to 100,000. When the third recurring unit is included, the number of units may be an integer in the range of 1 to 100,000. It is to be understood that the incorporation of the individual units may be statistical, random, or in block, and may depend upon the method used to synthesize the polymeric hydrogel 14.

In other examples of the polymeric hydrogel 14, the first recurring unit of formula (I) may be replaced with a heterocyclic azido group of formula (III):

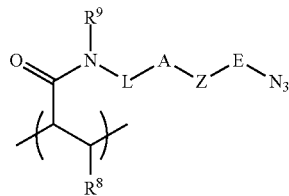

wherein $R^8$ is H or a C1-C6 alkyl; $R^9$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 carbon-containing ring members present as a single cyclic structure or a fused structure. Some specific examples of Z include pyrrolidinyl, pyridinyl, or pyrimidinyl.

In one example, formula (III) is the first recurring unit and formula (II) is the second recurring unit. In another example, formula (III) is the first recurring unit, one example of formula (II) is the second recurring unit, and a different example of formula (III) is the third recurring unit.

It is to be understood that other polymeric hydrogels 14 may be used, as long as they are functionalized to graft oligonucleotide primers 16A, 16B thereto and are capable of attaching to the plasmonic core 12, 12'. Some examples of suitable hydrogels 14 include functionalized polysilanes, such as norbornene silane, azido silane, alkyne functionalized silane, amine functionalized silane, maleimide silane, or any other polysilane having functional groups that can attach the oligonucleotide primers 16A, 16B. Other examples of suitable hydrogels 14 include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymeric hydrogels include mixed copolymers of acrylamides and acrylates. A variety of polymer architectures containing acrylic monomers (e.g., acrylamides, acrylates etc.) may be utilized in the examples disclosed herein, such as highly branched polymers, including dendrimers. For example, the monomers (e.g., acrylamide, etc.) may be incorporated, either randomly or in block, into the branches (arms) of a dendrimer.

An example of the dendrimeric polymeric hydrogel 14 includes a dendritic core with recurring units of formulas (II) and (III) in the arms extending from the core. The dendritic core may have anywhere from 3 arms to 30 arms.

The dendritic core may be any multi-functional component that enables a controlled polymerization mechanism, which leads to a defined arm length in the polymer structure and an at least substantially uniform arm length between polymer structures. In an example, the arms of the dendritic core are identical to each other.

The central molecule/compound of the dendritic core may be any multi-functional molecule, such as macrocycles (e.g., cyclodextrins, porphyrins, etc.), extended pi-systems (e.g., perylenes, fullerenes, etc.), metal-ligand complexes, polymeric cores, etc. Some specific examples of the central molecule/compound of the dendritic core include a phenyl group, benzoic acid, pentaerythritol, a phosphazene group, etc.

The dendritic core includes arms that extend from the central molecule/compound. Each arm may include a group that enables the monomers of formula (II) and (III) to be incorporated. In one example, a thiocarbonylthio group is included in each arm, and thus includes a reversible addition-fragmentation chain transfer agent (a RAFT agent). In another example, the dendritic core includes an atom transfer radical polymerization (ATRP) initiator in each arm. In still another example, the dendritic core includes a nitroxide (aminooxyl) mediated polymerization (NMP) initiator in each arm.

It is to be understood that functional groups in one or more of the recurring units of the polymeric hydrogel 14 are capable of attaching the primers 16A, 16B. These functional groups (e.g., $R^2$, $NH_2$, $N_3$, etc.) may be located in the side chains of the linear or branched polymeric hydrogels 24 or in the arms of the dendrimer polymeric hydrogels 14. These functional groups may be introduced as part of the monomer(s) used in copolymerization. To control the number of primer 16A, 16B anchorage points, the monomer bearing the functional group may be increased or decreased. These functional groups may alternatively be introduced after copolymerization.

The thickness of the polymeric hydrogel 14 on the plasmonic nanostructure core 12, 12' ranges from about 10 nm to about 200 nm. The polymeric hydrogel 14 can be in a dry state or can be in a swollen state, where it uptakes liquid. The 10 nm thickness represents the polymeric hydrogel 14 in the fully dry state, and the 200 nm thickness represents the polymeric hydrogel 14 in the fully swollen state. The thickness of the polymeric hydrogel 14 helps to ensure that a majority of the primers 16A, 16B graft at the desired distances from the plasmonic nanostructure core 12, 12'.

The weight average molecular weight of polymeric hydrogel 14 (linear or branched) ranges from about 10 kDa to about 2,000 kDa. In other examples, the weight average molecular weight ranges from about 100 kDa to about 400 kDa. Increasing the molecular weight will increase the thickness of the coating, and thus the molecular weight also helps to ensure that a majority of the primers 16A, 16B graft at the desired distances from the plasmonic nanostructure core 12, 12'.

For the dendrimer version of the polymeric hydrogel 14, the branching number may also be used to achieve the desired thickness. Increasing the branching number will also increase the thickness of the coating, and thus the branching number also helps to ensure that a majority of the primers 16A, 16B graft at the desired distances from the plasmonic nanostructure core 12, 12'. In an example, the branching number ranges from 3 to 30.

The functionalized plasmonic nanostructure 10, 10' also includes the primers 16A, 16B. The polymeric hydrogel 14 provides a 3D network at the surface of the nanostructure core 12, 12', and thus some primers 16A, 16B are attached at different distances from the plasmonic nanostructure core 12, 12'.

Examples of the primers 16A, 16B include P5 and P7 primers, examples of which are used on the surface of commercial flow cells sold by Illumina Inc. for sequencing, for example, on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms. The P5 and P7 primers have a universal sequence for seeding and/or amplification purposes.

The immobilization of the primers 16A, 16B may be by single point covalent attachment at the 5' end of the primers 16A, 16B. The attachment will depend, in part, on the functional groups of the polymeric hydrogel 14. Examples of terminated primers that may be used include an alkyne terminated primer, a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, a phosphoramidite terminated primer, and a triazolinedione terminated primer. In some specific examples, a succinimidyl (NHS) ester terminated primer may be reacted with an amine of the polymeric hydrogel 14, an aldehyde terminated primer may be reacted with a hydrazine of the polymeric hydrogel 14, or an alkyne terminated primer may be reacted with an azide of the polymeric hydrogel 14, or an azide terminated primer may be reacted with an alkyne or DBCO (dibenzocyclooctyne) of the polymeric hydrogel 14, or an amino terminated primer may be reacted with an activated carboxylate group or NHS ester of the polymeric hydrogel 14, or a thiol terminated primer may be reacted with an alkylating reactant (e.g., iodoacetamine or maleimide) of the polymeric hydrogel 14, or a phosphoramidite terminated primer may be reacted with a thioether of the polymeric hydrogel 14. While several examples have been provided, it is to be understood that a functional group that can be attached to the primer 16A, 16B and that can attach to a functional group of the polymeric hydrogel 14 may be used.

At least some of the primers 16A, 16B are attached at different distances from the plasmonic nanostructure core 12, 12'. These distances may range from greater than 0 nm to about 20 nm. In another example, the distances range from about 2 nm to about 15 nm. These distances may also change when the polymeric hydrogel swells and dries. Some primers 16A, 16B may also be positioned further from the plasmonic nanostructure core 12, 12', depending, in part, upon the thickness of the polymeric hydrogel 14. In this example, the number/amount of primers 16A, 16B attached within the 0 nm to 20 nm distance range may be a random distribution, or determined by the Gaussian distribution, or determined by any other type of distribution.

The functionalized plasmonic nanostructure 10, 10' are also capable of anchoring to a capture site on a flow cell substrate. As such, the functionalized plasmonic nanostructures 10, 10' include some mechanism that is capable of attaching to the capture site. The mechanism may be chemical (e.g., a functional agent), electrostatic, or magnetic.

In some examples, the mechanism is a component of the functionalized plasmonic nanostructure 10, 10' that enables it to be anchored without further functionalization. For example, when the plasmonic nanostructure core 12, 12' includes a magnetic material as the mechanism, the functionalized plasmonic nanostructure 10, 10' may be anchored to a magnetic capture agent on the flow cell substrate. For another example, when the polymeric hydrogel 14 includes a reversibly chargeable functional group as the mechanism, the functionalized plasmonic nanostructure 10, 10' may be anchored to an electrostatic capture agent on the flow cell substrate.

In other examples, the mechanism is a functional agent that is added to the functionalized plasmonic nanostructure 10, 10' that enables it to be anchored on the flow cell substrate. As one example, a target nucleic acid may be grafted to the polymeric hydrogel 14 that is complementary to a capture oligonucleotide on the flow cell substrate. As other examples, a functional group for covalent attachment or a member of a binding pair may be introduced to one of the monomers used in polymerization, or grafted to the polymeric hydrogel 14 after polymerization, or chemically introduced to the polymeric hydrogel 14 after polymerization. Any of the mechanisms described herein for attaching the polymeric hydrogel 14 to the plasmonic nanostructure core 12, 12' may be used for attaching the functionalized plasmonic nanostructure 10, 10' to the capture site on the flow cell substrate, and will depend on the particular capture site.

Methods for Making the Functionalized Plasmonic Nanostructures

In some examples, the functionalized plasmonic nanostructures 10, 10' may be prepared by generating the polymeric hydrogel 14, coating the polymeric hydrogel 14 on the plasmonic nanostructure(s) 18, and grafting the primers 16A, 16B to the polymeric hydrogel 14.

As described herein, the polymeric hydrogel 14 is a co-polymer including the recurring acrylamide unit (formula (I)), or a dendrimer including the recurring acrylamide unit (formula (I)) in each arm.

To generate the linear co-polymer including recurring units of formula (I) and (II) or (II) and (III), suitable monomers are copolymerized. The monomers used will depend upon the desired structure for the resulting co-polymer.

An example of a monomer for generating the recurring unit of formula (I) is shown at formula (IV):

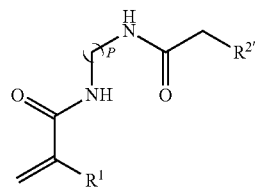

where $R^1$ may be any of the examples set forth herein for formula (I), and $R^{2'}$ may be any of the examples set forth herein for formula (I) or may be a halogen (e.g., bromine, fluorine, and iodine etc.).

An example of a monomer for generating the recurring unit of formula (II) is shown at formula (V):

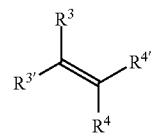

where $R^3$, $R^{3'}$, $R^4$, and $R^{4'}$ may be any of the examples set forth herein for formula (II).

An example of a monomer for generating the recurring unit of formula (III) is shown at formula (VI):

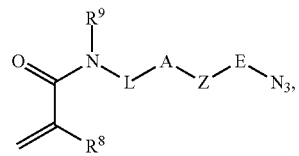

where $R^8$ and $R^9$, L, A, Z, and E may be any of the examples set forth herein for formula (III).

Any example of the monomers of formulas (IV) and (V) or formulas (V) and (VI) may be mixed together with an initiator to form a reaction mixture. Any suitable initiator may be used, e.g., a water soluble radical initiator, such as potassium persulfate or 4,4'-Azobis(4-cyanovaleric acid), a nitroxide mediated initiator, such as 2,2,6,6-Tetramethylpiperidinyloxy (TEMPO), di-tert-butyl nitroxide, 2,2,5-Trimethyl-4-phenyl-3-azahexane-3-nitroxide, β-phosphonylated nitroxide, etc.

The reaction mixture includes the monomers, the initiator, and water, a solvent, or a combination of water with the solvent. Example solvents include N-methyl-2-pyrollidone (NMP), dimethyl formamide (DMF), dimethyl sulfoxide (DMSO), acetonitrile (MeCN), methanol (MeOH), ethanol (EtOH), isopropyl alcohol (IPA), dioxane, acetone, dimethylacetamide (DMAc), or the like. The mixture may also include a buffer to at least substantially prevent undesirable changes in the pH. The pH of the reaction mixture may be acidic (<7). Examples of suitable buffers include TRIS (tris(hydroxymethyl)aminomethane or TRIZMA®), Bis-tris methane buffer, ADA buffer (a zwitterionic buffering agent), MES (2-ethanesulfonic acid), MOPS (3-(N-morpholino)propanesulfonic acid), or another acidic buffer.

The monomers of formulas (IV) and (V) or formulas (V) and (VI) may be present in a suitable weight ratio with respect to one another such that the desirable number of respective recurring units is introduced into the resulting copolymer. The initiator may be present in an amount that enables all of the monomers in the reaction mixture to copolymerize. In one example, the initiator may make up from about 0.005 wt % to about 5 wt % of the reaction mixture.

Copolymerization is carried out under suitable conditions. As an example, the temperature may range from about room temperature (e.g., 18° C.-25° C.) to about 150° C., and will depend upon the solvent, monomer, and choice of initiator. For example, when water alone is used, the temperature may be 90° C. or less. When a solvent or a combination of water and solvent is used, higher temperatures may be used. Some other example temperature ranges include from about 18° C. to about 130° C., from about 50° C. to about 75° C., etc. The time for the polymerization reaction may range from about 5 minutes to about 24 hours, e.g., 1 hour to 10 hours.

The temperature may be set so that the growing copolymer chain can continuously add the monomer units. In one example, polymerization may be quenched using a suitable quencher for the reaction taking place.

In some example methods, tetramethylethylenediamine may be added to the reaction mixture. The TeMED may be added prior to the initiation of copolymerization or as copolymerization is taking place. As a result of this reaction, at least some of the $R^2$ groups of formula (I) or the $N_3$ groups of formula (III) are replaced with TeMED, which provides a branching site in the copolymer chain. As such, at least some of the copolymer chains branch with each other.

One or more of the monomers (formulas (IV), (V), (VI)) may include the functional group(s) for attachment to the plasmonic nanoparticle core 12, 12', the functional group(s) for primer 16A, 16B grafting, and/or the functional group(s) for attaching to a capture site of a flow cell.

Alternatively, functional group(s) of recurring units of the copolymer (polymeric hydrogel 14) may be transformed after copolymerization.

In one example, transformation may involve grafting a desirable moiety to the polymeric hydrogel 14. For example, biotin and/or a NiNTA ligand may be grafted to enable attachment of the polymeric hydrogel 14 to the plasmonic nanoparticle core 12, 12' and/or attachment of the functionalized plasmonic nanoparticle 10, 10' to the capture site of a flow cell.

In another example, transformation may involve further reaction with the copolymer (polymeric hydrogel 14) to chemically modify the polymeric hydrogel 14 with the desirable moiety. For example, if the monomer (IV) and the resulting recurring unit includes a halogen (e.g., bromine) as $R^{2'}$, the copolymer may be exposed to $NaN_3$ and heating to replace the halogen with an azido. The azido may be used for primer 16A, 16B grafting, core 12, 12' attachment, and/or capture site anchoring. Other chemical modifications may take place to introduce a carboxylic acid, an amine, a sulfide, or any other functional groups for attachment to the plasmonic nanoparticle core 12, 12', for primer 16A, 16B grafting, and/or for attaching to the capture site.

When the polymeric hydrogel 14 is coated on the plasmonic nanostructure(s) 18 making up the core 12, 12' (as opposed to being grown from the core 12, 12'), it is to be understood that the molecular weight and branching numbers of the polymeric hydrogel 14 may be used to achieve the desired thickness. Increasing the molecular weight and/or the branching number will increase the thickness of the coating.

Once generated, the polymeric hydrogel 14 may be coated on the plasmonic nanoparticle core 12, 12' using any suitable deposition techniques. Examples of suitable deposition techniques include dip coating, dunk coating, spin coating, spray coating, puddle dispensing, ultrasonic spray coating, etc. In an example, the plasmonic nanoparticle core 12, 12' may be suspended in the polymeric hydrogel 14 and exposed to conditions (e.g., heat) that will initiate the attachment of the polymeric hydrogel 14 to the plasmonic nanoparticle core 12, 12'.

Once the polymeric hydrogel 14 is coated on the plasmonic nanostructure core 12, 12', the primers 16A, 16B may be grafted to the polymeric hydrogel 14. Grafting may involve dunk coating, which involves immersing the plasmonic nanostructure core 12, 12' with the polymeric hydrogel 14 thereon in a primer solution or mixture, which may include the primer(s) 16A, 16B, water, a buffer, and a catalyst. Other grafting techniques may involve spray coating, puddle dispensing, or another suitable method that will attach the primer(s) 16A, 16B to the polymeric hydrogel 14. With any of the grafting methods, the primers 16A, 16B react with reactive groups of the polymeric hydrogel 14.

In other examples, the primers 16A, 16B may be grafted to the polymeric hydrogel 14 before it is deposited on the plasmonic nanostructure core 12, 12'. The plasmonic nanoparticle core 12, 12' may be suspended in the pre-grafted polymeric hydrogel 14 and exposed to conditions (e.g., heat) that will initiate the attachment of the pre-grafted polymeric hydrogel 14 to the plasmonic nanoparticle core 12, 12'. In these examples, additional grafting is not performed.

To generate the dendrimer example of the polymeric hydrogel 14, which includes recurring units of formula (I) and (II) or (II) and (III) in the arms, reversible addition-fragmentation chain transfer (RAFT) polymerization, atom transfer radical polymerization (ATRP), nitroxide mediated radical (NMP) polymerization in combination with RAFT or ATRP, NMP with an additional cross-linking step, cobalt-mediated polymerization, group transfer polymerization (GTP), ring opening polymerization (ROP), or any other polymerization process that either directly or indirectly yields the multi-arm architecture and the incorporation of the acrylamide monomers (statistically, randomly, alternatingly, or in block) into each arm may be used.

In an example, a mixture of the monomers (IV) and (V) or (V) and (VI) are polymerized in the presence of the dendritic core, which includes an appropriate chain transfer agent or initiator in each arm extending therefrom. The mixture of the monomers (IV) and (V) or (V) and (VI) may include water and/or any example of the solvent set forth herein (e.g., N-methyl-2-pyrollidone (NMP), dimethyl formamide (DMF), dimethyl sulfoxide (DMSO), acetonitrile (MeCN), methanol (MeOH), ethanol (EtOH), isopropyl alcohol (IPA), dioxane, acetone, dimethylacetamide (DMAc), or the like). The mixture may also include any of the buffers set forth herein.

The polymerization reaction may take place at a temperature ranging from about 50° C. to about 80° C. for a time ranging from about 1 hour to about 48 hours. An initiator, including azo initiators, such as azobisisobutyronitrile or 2,2'-Azobis[2-(2-imidazolin-2-yl)propane]dihydrochloride (one commercially available example is VA-044 from Fuji-Film), may also be included in the mixture.

One or more of the monomers (formulas (IV), (V), (VI)) incorporated into the dendrimer may include the functional group(s) for attachment to the plasmonic nanoparticle core 12, 12', the functional group(s) for primer 16A, 16B grafting, and/or the functional group(s) for attaching to a capture site of a flow cell.

Alternatively, functional group(s) of recurring units of the dendrimer (polymeric hydrogel 14) may be transformed after polymerization or copolymerization.

In one example, transformation may involve grafting a desirable moiety to the dendrimeric polymeric hydrogel 14. For example, biotin and/or a NiNTA ligand may be grafted to enable attachment of the polymeric hydrogel 14 to the plasmonic nanoparticle core 12, 12' and/or attachment of the functionalized plasmonic nanoparticle 10, 10' to the capture site of a flow cell.

In another example, transformation may involve further reaction with the dendrimer (polymeric hydrogel 14) to chemically modify the polymeric hydrogel 14 with the desirable moiety. For example, if the monomer (IV) and the resulting recurring unit includes a halogen (e.g., bromine) as $R^{2'}$, the copolymer may be exposed to $NaN_3$ and heating to replace the halogen with an azido. The azido may be used for primer 16A, 16B grafting, core 12, 12' attachment, and/or capture site anchoring. Other chemical modifications may take place to introduce a carboxylic acid, an amine, a sulfide, or any other functional groups for attachment to the plasmonic nanoparticle core 12, 12', for primer 16A, 16B grafting, and/or for attaching to the capture site.

Once generated, the dendrimeric polymeric hydrogel 14 may be coated on the plasmonic nanoparticle core 12, 12' using any suitable deposition techniques. Examples of suitable deposition techniques include dip coating, dunk coating, spin coating, spray coating, puddle dispensing, ultrasonic spray coating, etc. In an example, the plasmonic nanoparticle core 12, 12' may be suspended in the dendrimeric polymeric hydrogel 14 and exposed to conditions (e.g., heat) that will initiate the attachment of the polymeric hydrogel 14 to the plasmonic nanoparticle core 12, 12'.

Once the dendrimeric polymeric hydrogel 14 is attached to the plasmonic nanostructure core 12, 12', the primers 16A, 16B may be grafted to the polymeric hydrogel 14. Grafting may performed as described herein. With any of the grafting methods, the primers 16A, 16B may react with reactive groups in each of the arms of the dendrimeric polymeric hydrogel 14.

In other examples, the primers 16A, 16B may be grafted to the dendrimeric polymeric hydrogel 14 before it is deposited on the plasmonic nanostructure core 12, 12'. The plasmonic nanoparticle core 12, 12' may be suspended in the pre-grafted dendrimeric polymeric hydrogel 14 and exposed to conditions (e.g., heat) that will initiate the attachment of the pre-grafted dendrimeric polymeric hydrogel 14 to the plasmonic nanoparticle core 12, 12'. In these examples, additional grafting is not performed.

In still other examples of the method, polymerization of the polymeric hydrogel 14 takes place from the plasmonic nanostructure core 12, 12'. This may be achieved by reversible addition-fragmentation chain-transfer (RAFT) polymerization directly on the plasmonic nanostructure core 12, 12'. This method generates polymeric hydrogel 14 brushes that extend from the core 12, 12'.

In these examples, the plasmonic nanostructure(s) 18 that are to make up the core 12, 12' may first be functionalized with an amine. The amine is used to attach a chain transfer agent (CTA) that can initiate polymerization.

The CTA-functionalized core 12, 12' may then be mixed with the monomers (IV) and (V) or (V) and (VI). The mixture of the monomers (IV) and (V) or (V) and (VI) may include water and/or the solvent(s) set forth herein. The mixture may also include any example of the buffer.

The polymerization reaction may take place at a temperature ranging from about room temperature (e.g., about 20° C.) to about 100° C. for a time ranging from about 1 hour to about 48 hours. In another example, the polymerization reaction may take place at a temperature ranging from about 50° C. to about 80° C.

One or more of the monomers (formulas (IV), (V), (VI)) incorporated into the polymeric hydrogel 14 brushes extending from the core 12, 12' may include the functional group(s) for primer 16A, 16B grafting, and/or the functional group(s) for attaching to a capture site of a flow cell.

Alternatively, functional group(s) of recurring units of the polymeric hydrogel 14 brushes may be transformed after polymerization or copolymerization. In one example, transformation may involve grafting a desirable moiety to the polymeric hydrogel 14. For example, biotin and/or a NiNTA ligand may be grafted to enable attachment of the functionalized plasmonic nanoparticle 10, 10' to the capture site of a flow cell. In another example, transformation may involve further reaction with the polymeric hydrogel 14 brushes to chemically modify the polymeric hydrogel 14 brushes with the desirable moiety. For example, if the monomer (IV) and the resulting recurring unit includes a halogen (e.g., bromine) as $R^{2'}$, the copolymer may be exposed to $NaN_3$ and heating to replace the halogen with an azido. The azido may be used for primer 16A, 16B grafting, core 12, 12' attachment, and/or capture site anchoring. Other chemical modifications may take place to introduce a carboxylic acid, an amine, a sulfide, or any other functional groups for attaching to the capture site.

Polymerization of the monomers (VI) and (V) or (V) and (VI) directly from the core 12, 12' may be particularly desirable for controlling the thickness of the polymeric hydrogel 14 as polymerization can be ceased once the desirable thickness is achieved.

Once the polymeric hydrogel 14 is grown from the core 12, 12', the primers 16A, 16B may be grafted to the polymeric hydrogel 14 as described herein. With any of the grafting methods, the primers 16A, 16B may react with reactive groups in the polymeric hydrogel 14 brushes.

The functionalized plasmonic nanoparticles 10, 10' may be suspended in a liquid carrier. Any liquid carrier that does not solubilize the plasmonic nanoparticle core 12, 12' may be used. Examples of the liquid carrier include a buffer (e.g., a Tris-HCl buffer or 0.5× saline sodium citrate (SSC) buffer), acetic acid, acetone, acetonitrile, benzene, butanol, diethylene glycol, diethyl ether, dimethyl formamide, ethanol, glycerin, methane, pyridine, triethyl amine, etc. Surfactants/dispersants, such as sodium dodecyl sulfate (SDS), (CTAB) may also be included. This suspension may be used for off-flow cell template strand preparation and amplification, and then may be incorporated into a flow cell for sequencing. This suspension may also be introduced to the flow cell, and used for on-flow cell template strand preparation and amplification.

Flow Cells Including the Functionalized Plasmonic Nanostructures

Figure 2A:
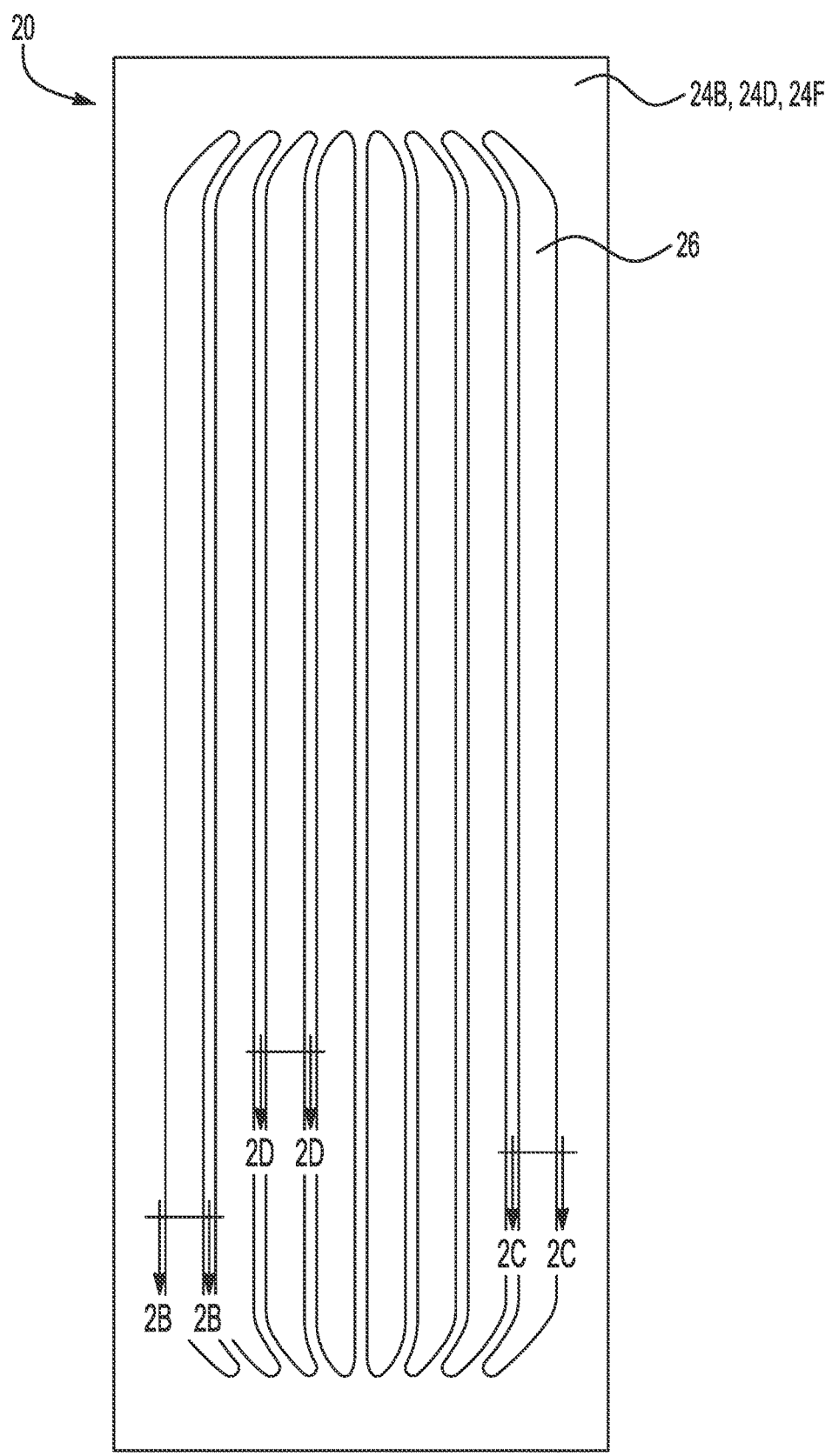
FIG. 2A is a top view of an example of a flow cell.
Figure 2B:
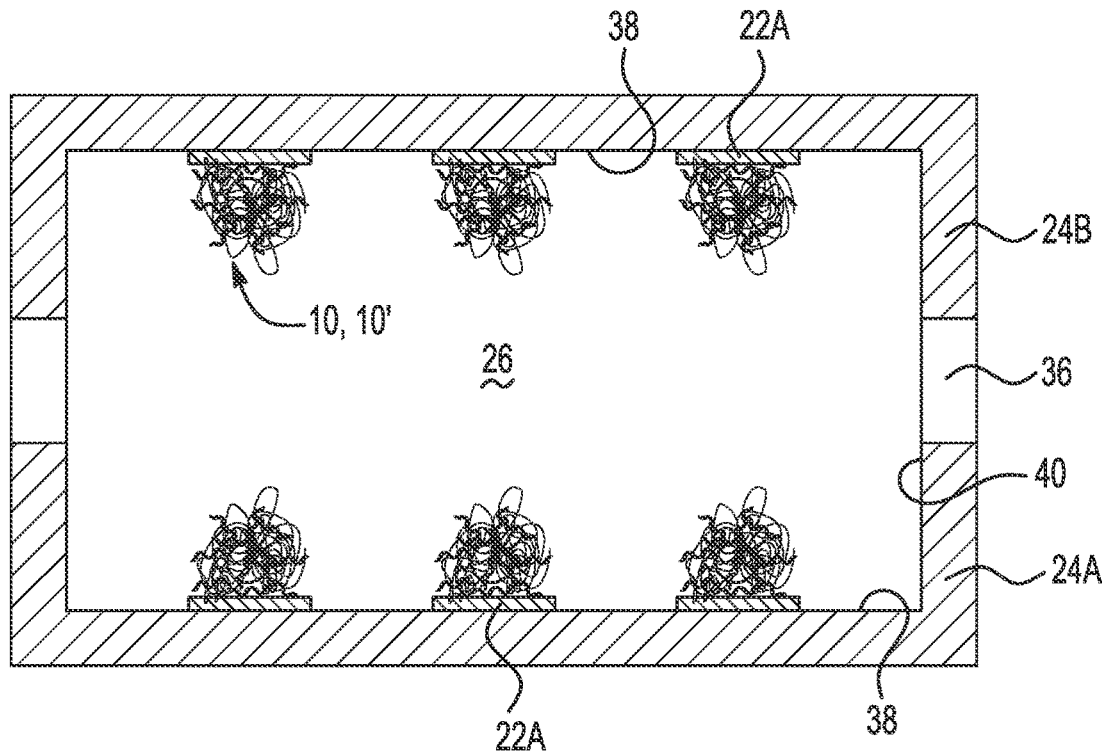
FIG. 2B is an enlarged, cross-sectional view, taken along the 2B-2B line of FIG. 2A, depicting one example the flow cell architecture including the functionalized plasmonic nanostructure anchored to a lane.
Figure 2C:
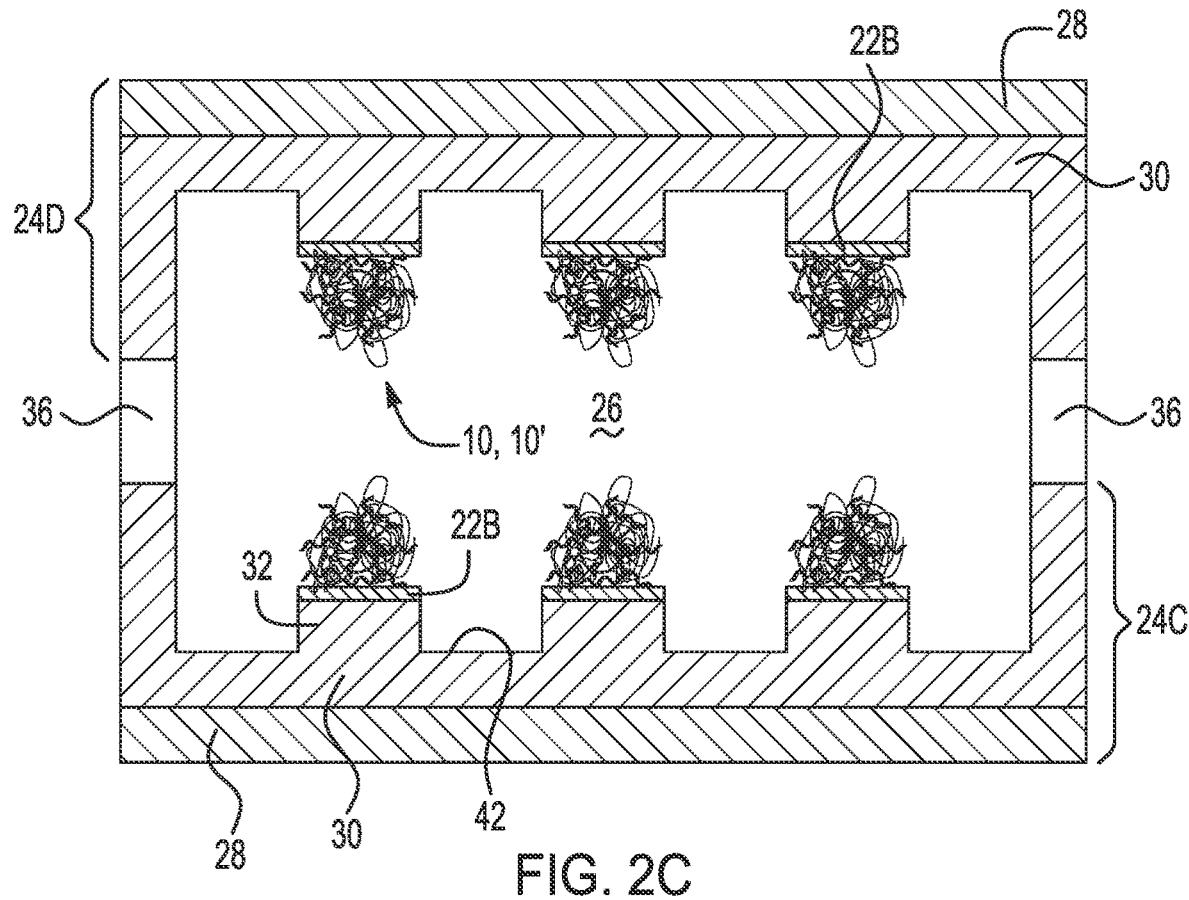
FIG. 2C is an enlarged, cross-sectional view, taken along the 2C-2C line of FIG. 2A, depicting another example the flow cell architecture including the functionalized plasmonic nanostructure anchored to posts.
Figure 2D:
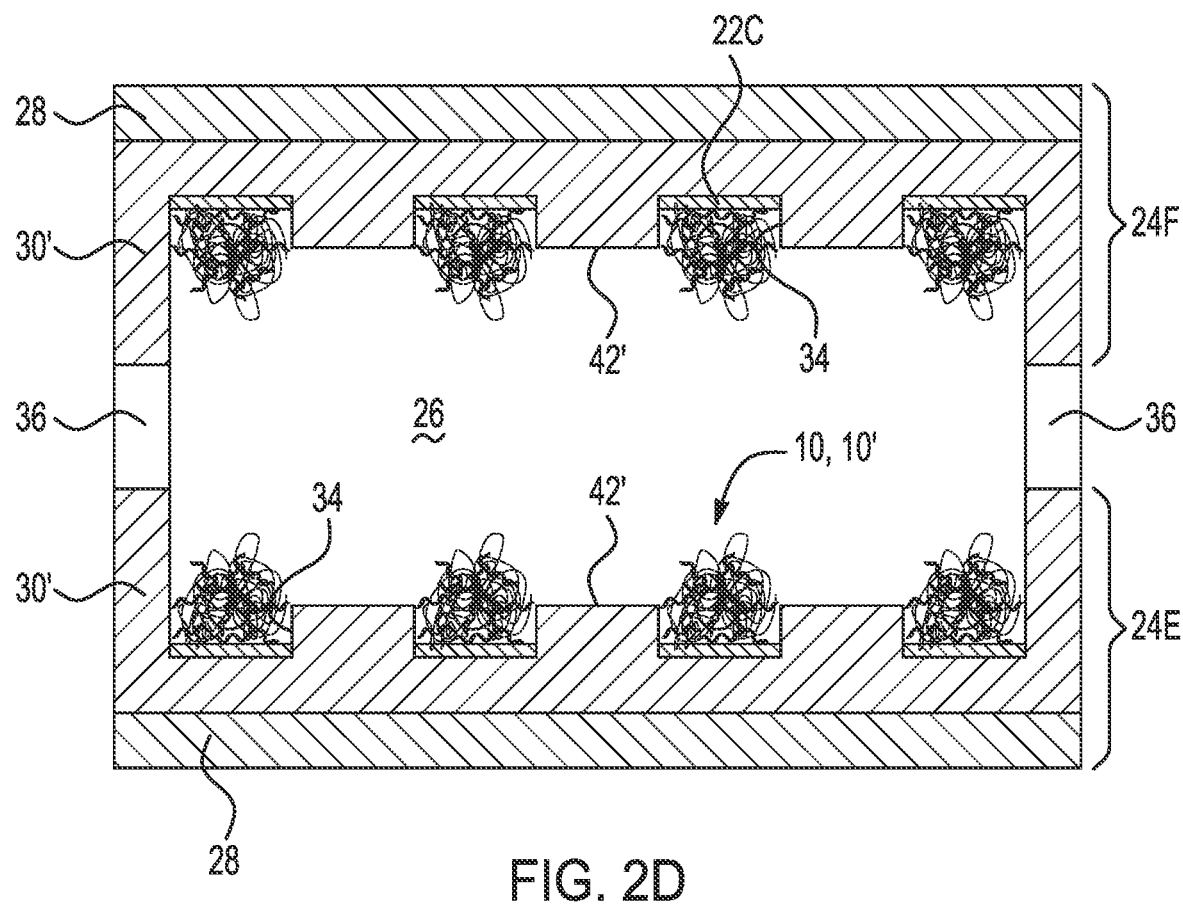
FIG. 2D is an enlarged, cross-sectional view, taken along the 2D-2D line of FIG. 2A, depicting yet another example the flow cell architecture including the functionalized plasmonic nanostructure anchored to depressions.

The functionalized plasmonic nanostructure 10, 10' may be used with any flow cell 20 (FIG. 2A) that includes capture sites 22 (FIG. 2B, FIG. 2C, FIG. 2D). An example of the flow cell 20 is depicted from the top view in FIG. 2A, and different examples of the flow cell architecture, including different capture sites 22A, 22B, 22C, are shown in FIG. 2B, FIG. 2C, and FIG. 2D.

A top view of an example of the flow cell 20 is shown in FIG. 2A. As will be discussed in reference to FIG. 2B, FIG. 2C and FIG. 2D, some examples of the flow cell 20 include two opposed substrates 24A, 24B or 24C, 24D, or 24E, 24F, each of which is configured with capture sites 22. In these examples, a flow channel 26 is defined between the two opposed substrates 24A, 24B or 24C, 24D, or 24E, 24F. In other examples, the flow cell 20 includes one substrate 24A or 24C or 24E configured with capture sites 22 and a lid attached to the substrate 24A or 24C or 24E. In these examples, the flow channel 26 is defined between the substrate 24A or 24C or 24E and the lid.

Different substrates 24A, 24B or 24C, 24D, or 24E, 24F are shown in FIG. 2B, FIG. 2C and FIG. 2D.

In the example shown in FIG. 2B, the substrates 24A, 24B are single layered structures. Examples of suitable single layered structures for the substrate 24A, 24B include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HfO_2$), carbon, metals, inorganic glasses, or the like.

In the examples shown in FIG. 2C and FIG. 2D, the substrates 24C, 24D, 24E, 24F are multi-layered structures. The multi-layered structures of the substrates 24C, 24D, 24E, 24F include a base support 28 and a patterned material 30 or 30' on the base support 28.

The base support 28 may be any of the examples set forth herein for the single layered structure of the substrate 24A, 24B.

The patterned material 30 or 30' may be any material that is capable of being patterned with posts 32 (FIG. 2B) or depressions 34 (FIG. 2C).

In an example, the patterned material 30, 30' may be an inorganic oxide that is selectively applied to the base support 28, e.g., via vapor deposition, aerosol printing, or inkjet printing, in the desired pattern. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

In another example, the patterned material 30, 30' may be a resin matrix material that is applied to the base support 28 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane-based resin, a non-polyhedral oligomeric silsesquioxane epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (commercially available under the tradename FOSS® from Hybrid Platics) refers to a chemical composition that is a hybrid intermediate (e.g., $RSiO_{1.5}$) between that of silica ($SiO_2$) and silicone ($R_2SiO$). An example of polyhedral oligomeric silsesquioxane can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for polyhedral oligomeric silsesquioxane include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units. The average cage content can be adjusted during the synthesis, and/or controlled by purification methods, and a distribution of cage sizes of the monomeric unit(s) may be used in the examples disclosed herein.

In an example, the substrates 24A, 24B, or 24C, 24D, or 24E, 24F (whether single or multi-layered) may be round and have a diameter ranging from about 2 mm to about 300 mm, or may be a rectangular sheet or panel having its largest dimension up to about 10 feet (~3 meters). In an example, the substrate 24A, 24B, or 24C, 24D, or 24E, 24F is a wafer having a diameter ranging from about 200 mm to about 300 mm. Wafers may subsequently be diced to form an individual flow cell substrate. In another example, the substrate 24A, 24B, or 24C, 24D, or 24E, 24F is a die having a width ranging from about 0.1 mm to about 10 mm. While example dimensions have been provided, it is to be understood that a substrate 24A, 24B, or 24C, 24D, or 24E, 24F with any suitable dimensions may be used. For another example, a panel may be used that is a rectangular support, which has a greater surface area than a 300 mm round wafer. Panels may subsequently be diced to form individual flow cells.

The flow cell 20 also includes the flow channel 26. While several flow channels 26 are shown in FIG. 2A, it is to be understood that any number of channels 26 may be included in the flow cell 20 (e.g., a single channel 26, four channels 26, etc.). Each flow channel 26 may be isolated from each other flow channel 26 in a flow cell 20 so that fluid introduced into any particular flow channel 26 does not flow into any adjacent flow channel 26.

A portion of the flow channel 26 may be defined in the substrate 24A, 24B, or 24C, 24D, or 24E, 24F using any suitable technique that depends, in part, upon the material(s) of the substrate 24A, 24B, or 24C, 24D, or 24E, 24F. In one example, a portion of the flow channel 26 is etched into a glass substrate, such as substrate 24A, 24B. In another example, a portion of the flow channel 26 may be patterned into a resin matrix material of a multi-layered structure using photolithography, nanoimprint lithography, etc. A separate material (e.g., material 36 in FIG. 2B, FIG. 2C, and FIG. 2D) may be applied to the substrate 24A, 24B, or 24C, 24D, or 24E, 24F so that the separate material 36 defines at least a portion of the walls of the flow channel 26.

In an example, the flow channel 26 has a substantially rectangular configuration with rounded ends. The length and width of the flow channel 26 may be smaller, respectively, than the length and width of the substrate 24A, 24B, or 24C, 24D, or 24E, 24F so that a portion of the substrate surface surrounding the flow channel 26 is available for attachment to another substrate 24A, 24B, or 24C, 24D, or 24E, 24F or a lid. In some instances, the width of each flow channel 26 can be at least about 1 mm, at least about 2.5 mm, at least about 5 mm, at least about 7 mm, at least about 10 mm, or more. In some instances, the length of each flow channel 26 can be at least about 10 mm, at least about 25 mm, at least about 50 mm, at least about 100 mm, or more. The width and/or length of each flow channel 26 can be greater than, less than or between the values specified above. In another example, the flow channel 26 is square (e.g., 10 mm×10 mm).

The depth of each flow channel 26 can be as small as a few monolayers thick, for example, when microcontact, aerosol, or inkjet printing is used to deposit the separate material 36 that defines the flow channel walls. In other examples, the depth of each flow channel 26 can be about 1 µm, about 10 µm, about 50 µm, about 100 µm, or more. In an example, the depth may range from about 10 µm to about 100 µm. In another example, the depth is about 5 µm or less. It is to be understood that the depth of each flow channel 26 can also be greater than, less than or between the values specified above. The depth of the flow channel 26 may also vary along the length and width of the flow cell 20, e.g., when posts 32 or depressions 34 are used.

In the example shown in FIG. 2B, the substrate 24A, 24B has a substantially flat surface 38; and the plurality of capture sites 22A are positioned in a pattern across the substantially flat surface 38.

The substantially flat surface 38 may be the bottom surface of a lane 40 that is defined in the single layer substrate 24A, 24B. A lane 40 may also be defined in the patterned layer 30, 30' of a multi-layered substrate 24C, 24D, 24E, 24F. The lane 40 may be etched into the substrate or defined, e.g., by lithography or another suitable technique.

The plurality of capture sites 22A are positioned in a pattern across the substantially flat surface 38.

Many different patterns for the capture sites 22A may be envisaged, including regular, repeating, and non-regular patterns. In an example, the capture sites 22A are disposed in a hexagonal grid for close packing and improved density. Other layouts may include, for example, rectilinear (rectangular) layouts, triangular layouts, and so forth. In some examples, the layout or pattern can be an x-y format of capture sites 22A that are in rows and columns. In some other examples, the layout or pattern can be a repeating arrangement of capture sites 22A separated by regions of the substantially flat substrate 38. In still other examples, the layout or pattern can be a random arrangement of capture sites 22A. The pattern may include stripes, swirls, lines, triangles, rectangles, circles, arcs, checks, diagonals, arrows, and/or squares.

The layout or pattern of the capture sites 22A may be characterized with respect to the density of the capture sites 22A (e.g., number of capture sites 22A) in a defined area. For example, the capture sites 22A may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density of capture sites 22A can be between one of the lower values and one of the upper values selected from the ranges above. As examples, a high density array may be characterized as having capture sites 22A separated by less than about 100 nm, a medium density array may be characterized as having capture sites 22A separated by about 400 nm to about 1 µm, and a low density array may be characterized as having capture sites 22A separated by greater than about 1 µm. While example densities have been provided, it is to be understood that any suitable densities may be used. In some instances, it may be desirable for the spacing between capture sites 22A to be even greater than the examples listed herein.

The layout or pattern of the capture sites 22A may also or alternatively be characterized in terms of the average pitch, or the spacing from the center of one capture site 22A to the center of an adjacent capture site 22A (center-to-center to-center spacing) or from the left edge of one capture site 22A to the right edge of an adjacent capture site 22A (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of capture sites 22A can be between one of the lower values and one of the upper values selected from the ranges above. In an example, the capture sites 22A have a pitch (center-to-center spacing) of about 1.5 µm. While example average pitch values have been provided, it is to be understood that other average pitch values may be used.

The capture sites 22A may have any suitable shape, geometry and dimensions, which may depend, at least in part, on the functionalized plasmonic nanoparticle 10, 10' that is to be captured by the capture site 22A.

The capture sites 22A may be chemical capture sites, electrostatic captures sites, or magnetic capture sites.

Chemical capture sites include any example of the chemical capture agent set forth herein that can be deposited on or otherwise attached to predefined locations of the substantially flat surface 38. In one example, the chemical capture agent may be deposited, e.g., using microcontact printing, aerosol printing, etc., in a desirable location on the substantially flat surface 38 to form the capture sites 22A. In another example, a mask (e.g., a photoresist) may be used to define the space/location where the chemical capture agent will be deposited. The chemical capture agent may then be deposited, and the mask removed (e.g., via lift-off, dissolution, or another suitable technique). In this example, the chemical capture agent may form a monolayer or thin layer of the chemical capture agent. In still another example, a polymer grafted with capture nucleic acids may be selectively applied to the substantially flat surface 38 to form the chemical captures sites.

Electrostatic captures sites include any example of the electrostatic capture agents set forth herein that can be deposited on predefined locations of the substantially flat surface 38. For example, electrode materials may be deposited using chemical vapor deposition, masking and deposition, or another suitable technique to form the capture sites 22A. When electrostatic capture sites are used, the substrate 24A, 24B may include additional circuitry to address the individual capture sites 22A.

Magnetic capture sites include any example of the magnetic capture agent set forth herein that can be deposited on predefined locations of the substantially flat surface 38. For example, magnetic materials may be deposited using chemical vapor deposition, masking and deposition, or another suitable technique to form the capture sites 22A.

In the example of FIG. 2B, areas of the substantially flat surface 38 that do not contain the capture sites 22A function as interstitial regions between the capture sites 22A.

In the example shown in FIG. 2C, the substrate 24C, 24D includes posts 32 separated by interstitial regions 42; and a capture site 22B is positioned over each of the posts 32.

Each post 32 is a three-dimensional structure that extends outward (upward) from an adjacent surface. The post 32 is thus a convex region with respect to the interstitial regions 42 that surround the posts 32. Posts 32 may be formed in or on a substrate 24C, 24D. In FIG. 2C, the posts 32 are formed in the substrate 24C, 24D. When the post 32 is formed "in the substrate" 24C, 24D, it is meant that the layer 30 is patterned (e.g., via etching, photolithography, imprinting, etc.,) so that the resulting posts 32 extend above the adjacent surrounding interstitial regions 42. Alternatively, when the post 32 is formed "on the substrate" 24C, 24D, it is meant that an additional material may be deposited on the substrate (e.g., single layer substrate 24A, 24B) so that it extends above the underlying substrate.

The layout or pattern of the posts 32 may be any of the examples set forth herein for the capture sites 22A. The layout or pattern of the posts 32 may be characterized with respect to the density of the posts 32 (e.g., number of posts 32) in a defined area. Any of the densities set forth for the capture sites 22A may be used for the posts 32. The layout or pattern of the posts 32 may also be characterized in terms of the average pitch, or the spacing from the center of one post 32 to the center of an adjacent post 32 (center-to-center spacing) or from the left edge of one post 32 to the right edge of an adjacent post 32 (edge-to-edge spacing). Any of the average pitches set forth for the capture sites 22A may be used for the posts 32.

While any suitable three-dimensional geometry may be used for the posts 32, a geometry with an at least substantially flat top surface may be desirable so that the capture site 22B may be formed thereon. Example post geometries include a sphere, a cylinder, a cube, polygonal prisms (e.g., rectangular prisms, hexagonal prisms, etc.), or the like.

The size of each post 32 may also be characterized by its top surface area, height, and/or diameter.

The top surface area of each post 32 can be selected based upon the size of the functionalized plasmonic nanoparticle 10, 10' that is to be anchored to the capture site 22B that is supported by the post 32. For example, the top surface area of each post 32 can be at least about $1 \times 10^{-4}$ $\mu m^2$, at least about $1 \times 10^{-3}$ $\mu m^2$, at least about 0.1 $\mu m^2$, at least about 1 $\mu m^2$, at least about 10 $\mu m^2$, at least about 100 $\mu m^2$, or more. Alternatively or additionally, the top surface area of each post 32 can be at most about $1 \times 10^4$ $\mu m^2$, at most about 100 $\mu m^2$, at most about 10 $\mu m^2$, at most about 1 $\mu m^2$, at most about 0.1 $\mu m^2$, at most about $1 \times 10^{-2}$ $\mu m^2$, or less. The area occupied by each depression opening can be greater than, less than or between the values specified above.

The height of each post 32 can depend upon the channel 26 dimensions. In an example, the height may be at least about 0.1 $\mu m$, at least about 0.5 $\mu m$, at least about 1 $\mu m$, at least about 10 $\mu m$, at least about 100 $\mu m$, or more. Alternatively or additionally, the height can be at most about $1 \times 10^3$ $\mu m$, at most about 100 $\mu m$, at most about 10 $\mu m$, or less. In some examples, the depth is about 0.4 $\mu m$. The height of each post 32 can be greater than, less than or between the values specified above.

In some instances, the diameter or length and width of each post 32 can be at least about 50 nm, at least about 0.1 $\mu m$, at least about 0.5 $\mu m$, at least about 1 $\mu m$, at least about 10 $\mu m$, at least about 100 $\mu m$, or more. Alternatively or additionally, the diameter or length and width can be at most about $1 \times 10^3$ $\mu m$, at most about 100 $\mu m$, at most about 10 $\mu m$, at most about 1 $\mu m$, at most about 0.5 $\mu m$, at most about 0.1 $\mu m$, or less (e.g., about 50 nm). In some examples, the diameter or length and width is about 0.4 $\mu m$. The diameter or length and width of each post 32 can be greater than, less than or between the values specified above.

In the example shown in FIG. 2C, the capture site 22B is positioned on each of the posts 32. The capture sites 22B may be chemical capture sites, electrostatic captures sites, or magnetic capture sites.

Chemical capture sites include any example of the chemical capture agent set forth herein that can be deposited on or otherwise attached to the top surface of each post 32. In one example, the chemical capture agent may be deposited, e.g., using microcontact printing, aerosol printing, etc., on each post 32 to form the capture site 22B. In another example, a mask (e.g., a photoresist) may be used to cover the interstitial regions 42 and not the posts 32. The chemical capture agent may then be deposited on the exposed posts 32, and the mask removed (e.g., via lift-off, dissolution, or another suitable technique). In this example, the chemical capture agent may form a monolayer or thin layer of the chemical capture agent on the post 32. In still another example, a polymer grafted with capture nucleic acids may be selectively applied to the top surface of each post 32 to form the chemical captures sites.

Electrostatic captures sites include any example of the electrostatic capture agent set forth herein that can be deposited on the top surface of each post 32. For example, electrode materials may be deposited using chemical vapor deposition, masking and deposition, or another suitable technique to form the capture sites 22B. When electrostatic capture sites are used, the substrate 24C, 24D may include additional circuitry to address the individual capture sites 22B.

Magnetic capture sites include any example of the magnetic capture agent set forth herein that can be deposited on the top surface of each post 32. For example, magnetic materials may be deposited using chemical vapor deposition, masking and deposition, or another suitable technique to form the capture sites 22B.

In the example shown in FIG. 2D, the substrate 24E, 24F includes depressions 34 separated by interstitial regions 42'; and a capture site 22C is positioned in each of the depressions 34.

Each depression 34 is a three-dimensional structure that extends inward (downward) from an adjacent surface. The depression 34 is thus a concave region with respect to the interstitial regions 42' that surround the depressions 34. Depressions 34 may be formed in a substrate 24E, 24F. In the example shown in FIG. 2D, the layer 30' is patterned (e.g., via etching, photolithography, imprinting, etc.,) to define the depressions 34 so that the interstitial regions 42' extend above and surround the adjacent depressions 34.

The layout or pattern of the depressions 34 may be any of the examples set forth herein for the capture sites 22A. The layout or pattern of the depressions 34 may be characterized with respect to the density of the depressions 34 (e.g., number of depressions 34) in a defined area. Any of the densities set forth for the capture sites 22A may be used for the depressions 34. The layout or pattern of the depressions 34 may also be characterized in terms of the average pitch, or the spacing from the center of one depression 34 to the center of an adjacent depression 34 (center-to-center spacing) or from the left edge of one depression 34 to the right edge of an adjacent depression 34 (edge-to-edge spacing). Any of the average pitches set forth for the capture sites 22A may be used for the depressions 34.

While any suitable three-dimensional geometry may be used for the depressions 34, a geometry with an at least substantially flat bottom surface may be desirable so that the capture site 22C may be formed thereon. Example depression geometries include a sphere, a cylinder, a cube, polygonal prisms (e.g., rectangular prisms, hexagonal prisms, etc.), or the like.

The size of each depression 34 may be characterized by its volume, opening area, depth, and/or diameter.

Each depression 34 can have any volume that is capable of receiving the material of the capture site 22C. For example, the volume can be at least about $1 \times 10^{-3}$ μm$^3$, at least about $1 \times 10^{-2}$ μm$^3$, at least about 0.1 μm$^3$, at least about 1 μm$^3$, at least about 10 μm$^3$, at least about 100 μm$^3$, or more. Alternatively or additionally, the volume can be at most about $1 \times 10^4$ μm$^3$, at most about $1 \times 10^3$ m$^3$, at most about 100 μm$^3$, at most about 10 μm$^3$, at most about 1 μm$^3$, at most about 0.1 μm$^3$, or less.

The area occupied by each depression opening can be selected based on the size of the functionalized plasmonic nanoparticles 10, 10' to be anchored by the capture site 22C. It may be desirable for the functionalized plasmonic nanoparticle 10, 10' to enter the depression 34, and thus the area occupied by the depression opening may be bigger than the size of the functionalized plasmonic nanoparticle 10, 10'. For example, the area for each depression opening can be at least about $1 \times 10^{-3}$ μm$^2$, at least about $1 \times 10^{-2}$ μm$^2$, at least about 0.1 μm$^2$, at least about 1 μm$^2$, at least about 10 μm$^2$, at least about 100 μm$^2$, or more. Alternatively or additionally, the area can be at most about $1 \times 10^3$ μm$^2$, at most about 100 μm$^2$, at most about 10 μm$^2$, at most about 1 μm$^2$, at most about 0.1 μm$^2$, at most about $1 \times 10^{-2}$ μm$^2$, or less. The area occupied by each depression opening can be greater than, less than or between the values specified above.

The depth of each depression 34 is large enough to house at least the capture site 22C. In one example, the depression 34 may be filled with the capture site 22C. In this example, the functionalized plasmonic nanostructure 10, 10' becomes anchored to the capture site 22C but does not enter the depression 34. In another example, the depression 34 may be partially filled with the capture site 22C. In this example, the functionalized plasmonic nanostructure 10, 10' at least partially enters the depression 34 and becomes anchored to the capture site 22C in the depression 34. In an example, the depth may be at least about 0.1 μm, at least about 0.5 μm, at least about 1 μm, at least about 10 μm, at least about 100 μm, or more. Alternatively or additionally, the depth can be at most about $1 \times 10^3$ μm, at most about 100 μm, at most about 10 μm, or less. In some examples, the depth is about 0.4 μm. The depth of each depression 34 can be greater than, less than or between the values specified above.

In some instances, the diameter or length and width of each depression 34 can be at least about 50 nm, at least about 0.1 μm, at least about 0.5 μm, at least about 1 μm, at least about 10 μm, at least about 100 μm, or more. Alternatively or additionally, the diameter or length and width can be at most about $1 \times 10^3$ μm, at most about 100 μm, at most about 10 μm, at most about 1 μm, at most about 0.5 μm, at most about 0.1 μm, or less (e.g., about 50 nm). In some examples, the diameter or length and width is about 0.4 μm. The diameter or length and width of each depression 34 can be greater than, less than or between the values specified above.

In the example shown in FIG. 2D, the capture site 22C is positioned in each of the depressions 34. The capture sites 22C may be chemical capture sites, electrostatic captures sites, or magnetic capture sites.

Chemical capture sites include any example of the chemical capture agent set forth herein that can be deposited on or otherwise attached to the bottom surface of each depression 34. In one example, the chemical capture agent may be deposited, e.g., using microcontact printing, aerosol printing, etc., on each depression 34 to form the capture sites 22C. In another example, a mask (e.g., a photoresist) may be used to cover the interstitial regions 42' and not the depressions 34. The chemical capture agent may then be deposited in the exposed depression 34, and the mask removed (e.g., via lift-off, dissolution, or another suitable technique). In this example, the chemical capture agent may form a monolayer or thin layer of the chemical capture agent in the depression 34. In still another example, a polymer grafted with capture nucleic acids may be selectively applied to the bottom surface of each depression 34.

Electrostatic captures sites include any example of the electrostatic capture agent set forth herein that can be deposited on the bottom surface of each depression 34. For example, electrode materials may be deposited using chemical vapor deposition, masking and deposition, or another suitable technique to form the capture sites 22C. When electrostatic capture sites are used, the substrate 24E, 24F may include additional circuitry to address the individual capture sites 22C.

Magnetic capture sites include any example of the magnetic capture agent set forth herein that can be deposited on the bottom surface of each depression 34. For example, magnetic materials may be deposited using chemical vapor deposition, masking and deposition, or another suitable technique to form the capture sites 22C.

While the example architectures shown in FIG. 2B, FIG. 2C, and FIG. 2C depict the functionalized plasmonic nanostructures 10, 10' anchored at the captures sites 22A, 22B, 22C, it is to be understood that the flow cell 20 does not include the functionalized plasmonic nanostructures 10, 10' until they are introduced thereto, e.g., during sequencing.

Kits Including the Functionalized Plasmonic Nanostructures

Any example of the flow cell 20 and the functionalized plasmonic nanostructures 10, 10' may be part of a kit. An example of the kit includes the flow cell 20 including a plurality of capture sites 22 and a suspension including a liquid carrier and a plurality of the functionalized plasmonic nanostructures 10, 10' dispersed throughout the liquid carrier. Any example of the functionalized plasmonic nanostructures 10, 10' and any liquid carrier that does not solubilize the plasmonic nanoparticle core 12, 12' may be included in the suspension. In the kit, the mechanism of the functionalized plasmonic nanostructures 10, 10' is selected to be able to anchor the functionalized plasmonic nanostructures 10, 10' to the capture site 22 of the flow cell 20 in the kit.

Sequencing Method

When the functionalized plasmonic nanoparticles 10, 10' are to be used in sequencing, they may first be used for the generation of template nucleic acid strands that are to be sequenced.

At the outset of template strand formation, library templates may be prepared from any nucleic acid sample (e.g., a DNA sample or an RNA sample). The DNA nucleic acid sample may be fragmented into single-stranded, similarly sized (e.g., <1000 bp) DNA fragments. The RNA nucleic acid sample may be used to synthesize complementary DNA (cDNA), and the cDNA may be fragmented into single-stranded, similarly sized (e.g., <1000 bp) cDNA fragments. During preparation, adapters may be added to the ends of any of the fragments. Through reduced cycle amplification, different motifs may be introduced in the adapters, such as sequencing primer binding sites, indices, and regions that are complementary to the primers 16A, 16B on the functionalized plasmonic nanostructures 10, 10'. In some examples, the fragments from a single nucleic acid sample have the same adapters added thereto. The final library templates include the DNA or cDNA fragment and adapters at both ends. The DNA or cDNA fragment represents the portion of the final library template that is to be sequenced.

A plurality of library templates may be introduced to a plasmonic enhancing suspension, which includes the liquid carrier and the functionalized plasmonic nanostructures 10, 10' disclosed herein. Multiple library templates are hybridized, for example, to one of two types of primers 16A, 16B immobilized to the polymeric hydrogel 14 of the functionalized plasmonic nanostructures 10, 10'.

Amplification of the template nucleic acid strand(s) on the functionalized plasmonic nanostructures 10, 10' may be initiated to form functionalized plasmonic nanostructures 10, 10' with a cluster of the template strands. In one example, amplification involves cluster generating. In one example of cluster generation, the library templates are copied from the hybridized primers by 3' extension using a high-fidelity DNA polymerase. The original library templates are denatured, leaving the copies immobilized all around the functionalized plasmonic nanostructures 10, 10'. Isothermal bridge amplification or some other form of amplification may be used to amplify the immobilized copies. For example, the copied templates loop over to hybridize to an adjacent, complementary primer, and a polymerase copies the copied templates to form double stranded bridges, which are denatured to form two single stranded strands. These two strands loop over and hybridize to adjacent, complementary primers and are extended again to form two new double stranded loops. The process is repeated on each template copy by cycles of isothermal denaturation and amplification to create dense clonal clusters on the functionalized plasmonic nanostructures 10, 10'. Each cluster of double stranded bridges is denatured. In an example, the reverse strand is removed by specific base cleavage, leaving forward template strands. Clustering results in the formation of several template strands immobilized on the functionalized plasmonic nanostructures 10, 10' at different distances from the core 12, 12'. This example of clustering is referred to as bridge amplification, and is one example of the amplification that may be performed. It is to be understood that other amplification techniques may be used.

The functionalized plasmonic nanostructures 10, 10' may be washed to remove unreacted library templates, etc. and suspended in a fresh carrier liquid.

The suspension including the functionalized plasmonic nanostructures 10, 10', which now includes a cluster of the template strands, may then be introduced into the flow cell 20 including the plurality of capture sites 22A, 22B, 22C, whereby at least some of the functionalized plasmonic nanostructures 10, 10' respectively attach to at least some of the capture site 22A, 22B, 22C. As described herein, the functionalized plasmonic nanostructures 10, 10' include a functional agent, a reversibly chargeable functional group, or magnetic material that specifically binds, attaches, or is otherwise attracted (e.g., electrostatically, magnetically, etc.) to the capture site 22A, 22B, 22C. The suspension may be allowed to incubate for a predetermined time to allow the functionalized plasmonic nanostructures 10, 10' to become anchored. When electrostatic capture sites 22A, 22B, 22C are used, the individual sites 22A, 22B, 22C may be electrically addressed to move the functionalized plasmonic nanostructures 10, 10' toward individual capture sites 22A, 22B, 22C. In this example, the functionalized plasmonic nanostructures 10, 10' may include a reversibly chargeable functional group that can be converted from a neutral species to a charged species at a suitable pH. The charged species can be generated by adjusting the pH, and then attracted to the electrostatic capture sites 22A, 22B, 22C that are individually or globally addressed.

A wash cycle may be performed to remove any unanchored functionalized plasmonic nanostructures 10, 10'.

Sequencing primers may then be introduced to the flow cell 20. The sequencing primers hybridize to a complementary portion of the sequence of the template strands that are attached to the functionalized plasmonic nanoparticles 10, 10'. These sequencing primers render the template strands ready for sequencing.

An incorporation mix including labeled nucleotides may then be introduced into the flow cell 20, e.g., via an input port. In addition to the labeled nucleotides, the incorporation mix may include water, a buffer, and polymerases capable of nucleotide incorporation. When the incorporation mix is introduced into the flow cell 20, the mix enters the flow channel 26, and contacts the anchored and sequence ready functionalized plasmonic nanostructures 10, 10'.

The incorporation mix is allowed to incubate in the flow cell 20, and labeled nucleotides (including optical labels) are incorporated by respective polymerases into the nascent strands along the template strands on each of the functionalized plasmonic nanostructures 10, 10'. During incorporation, one of the labeled nucleotides is incorporated, by a respective polymerase, into one nascent strand that extends one sequencing primer and that is complementary to one of the template strands. Incorporation is performed in a template strand dependent fashion, and thus detection of the order and type of labeled nucleotides added to the nascent strand can be used to determine the sequence of the template strand. Incorporation occurs in at least some of the template strands across the ready functionalized plasmonic nanostructures 10, 10' during a single sequencing cycle.

The incorporated labeled nucleotides may include a reversible termination property due to the presence of a 3' OH blocking group, which terminates further sequencing primer extension once the labeled nucleotide has been added. After a desired time for incubation and incorporation, the incorporation mix, including non-incorporated labeled nucleotides, may be removed from the flow cell 20 during a wash cycle. The wash cycle may involve a flow-through technique, where a washing solution (e.g., buffer) is directed into, through, and then out of flow channel 26, e.g., by a pump or other suitable mechanism.

Without further incorporation taking place, the most recently incorporated labeled nucleotides can be detected through an imaging event. During the imaging event, an illumination system may provide an excitation light to the flow cell 20. The optical labels of the incorporated labeled nucleotides emit optical signals in response to the excitation light. At least some of the optical labels are positioned within signal enhancing proximity of the plasmonic nanostructure core 12, 12' of the functionalized plasmonic nanostructures 10, 10', and thus the plasmonic nanostructure core 12, 12' enhances these optical signals through plasmonic resonance. Due to the different distances of the template strands, and thus the different distances of the incorporated labeled nucleotides, it is to be understood that some optical signals may be enhanced while others are not enhanced in the same sequencing cycle. Moreover, the optical signals that are enhanced may vary from one sequencing cycle to the next, depending upon the distance of the incorporated labeled nucleotides, and specifically its optical label, from the plasmonic nanostructure cores 12, 12' in a given cycle.

After imaging is performed, a cleavage mix may then be introduced into the flow cell 20. In an example, the cleavage mix is capable of i) removing the 3' OH blocking group from the incorporated nucleotides, and ii) cleaving the optical label from the incorporated nucleotide. Examples of 3' OH blocking groups and suitable de-blocking agents/components in the cleavage mix may include: ester moieties that can be removed by base hydrolysis; allyl-moieties that can be removed with NaI, chlorotrimethylsilane and $Na_2S_2O_3$ or with Hg(II) in acetone/water; azidomethyl which can be cleaved with phosphines, such as tris(2-carboxyethyl)phosphine (TCEP) or tri(hydroxypropyl)phosphine (THP), acetals, such as tert-butoxy-ethoxy which can be cleaved with acidic conditions; MOM ($-CH_2OCH_3$) moieties that can be cleaved with $LiBF_4$ and $CH_3CN/H_2O$, 2,4-dinitrobenzene sulfenyl which can be cleaved with nucleophiles such as thiophenol and thiosulfate; tetrahydrofuranyl ether which can be cleaved with Ag(I) or Hg(II), and 3' phosphate which can be cleaved by phosphatase enzymes (e.g., polynucleotide kinase). Examples of suitable optical label cleaving agents/components in the cleavage mix may include: sodium periodate, which can cleave a vicinal diol; phosphines, such as tris(2-carboxyethyl)phosphine (TCEP) or tris(hydroxypropyl)phosphine (THP), which can cleave azidomethyl linkages; palladium and THP, which can cleave an allyl; bases, which can cleave ester moieties; or any other suitable cleaving agent.

Additional sequencing cycles may then be performed until the template strands are sequenced.

In other sequencing methods, the suspension of functionalized plasmonic nanoparticles 10, 10' may first be introduced into the flow cell 20 and exposed to conditions that help to anchor at least some of the plasmonic nanoparticles 10, 10' to the capture sites 22A, 22B, 22C. In these examples, the functionalized plasmonic nanoparticles 10, 10' do not have the cluster of template strands attached thereto. Rather, the library templates are prepared off-flow cell, and then are introduced into the flow cell for generation and amplification of the template nucleic acid strands on the already anchored plasmonic nanoparticles 10, 10'. In this example, any unattached library templates are removed from the flow cell prior to sequencing, and then sequencing may then be performed as described herein.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such values or sub-ranges were explicitly recited. For example, a range from about 2 mm to about 300 mm, should be interpreted to include not only the explicitly recited limits of from about 2 mm to about 300 mm, but also to include individual values, such as about 40 mm, about 250.5 mm, etc., and sub-ranges, such as from about 25 mm to about 175 mm, etc.

Furthermore, when "about" and/or "substantially" are/is utilized to describe a value, they are meant to encompass minor variations (up to +/− 10%) from the stated value.

While several examples have been described in detail, it is to be understood that the disclosed examples may be modified. Therefore, the foregoing description is to be considered non-limiting.

What is claimed is:

1. A functionalized plasmonic nanostructure, comprising:
   a plasmonic nanostructure core;
   a polymeric hydrogel attached to the plasmonic nanostructure core, the polymeric hydrogel having a thickness ranging from about 10 nm to about 200 nm;
   a plurality of two primers that together seed and amplify a template nucleic acid strand, the plurality of two primers being attached to side chains or arms of the polymeric hydrogel, wherein at least some of the plurality of primers are attached to the polymeric hydrogel at different distances from the plasmonic nanostructure core; and
   a mechanism to anchor the functionalized plasmonic nanostructure to a capture site of a flow cell.

2. The functionalized plasmonic nanostructure as defined in claim 1, wherein the plasmonic nanostructure core is selected from the group consisting of a gold nanostructure, a silver nanostructure, a tin nanostructure, a rhodium nanostructure, a ruthenium nanostructure, a palladium nanostructure, an osmium nanostructure, an iridium nanostructure, a platinum nanostructure, a chromium nanostructure, a copper nanostructure, a gallium arsenide nanostructure, a doped silicon nanostructure, an aluminum nanostructure, a magnesium nanostructure, a silver and gold composite nanostructure, and combinations thereof.

3. The functionalized plasmonic nanostructure as defined in claim 1, wherein:
   the polymeric hydrogel includes at least one acrylamide monomer unit; and
   the polymeric hydrogel is a linear polymeric hydrogel or a branched polymeric hydrogel.

4. The functionalized plasmonic nanostructure as defined in claim 1, wherein:
   the plasmonic nanostructure core is functionalized with an alkyne, and the polymeric hydrogel includes an azide that is attached to the alkyne; or the plasmonic nanostructure core is functionalized with an azide, and the polymeric hydrogel includes a dialkyne that is attached to the azide.

5. The functionalized plasmonic nanostructure as defined in claim 1, wherein the mechanism is a magnetic material in the plasmonic nanostructure core.

6. The functionalized plasmonic nanostructure as defined in claim 1, wherein the mechanism is a functional agent incorporated into the polymeric hydrogel, wherein the functional agent is selected from the group consisting of a target nucleic acid that is complementary to a capture nucleic acid on a flow cell and a member of a binding pair that is capable of binding to a second member of a binding pair that is attached to the flow cell.

7. The functionalized plasmonic nanostructure as defined in claim 1, wherein the mechanism is a reversibly chargeable functional group attached to the polymeric hydrogel.

8. The functionalized plasmonic nanostructure as defined in claim 1, wherein the different distances range from greater than 0 nm to about 20 nm.

9. A kit, comprising:
a flow cell including a plurality of capture sites, wherein each capture site is a magnetic capture site, or includes a chemical capture agent, or includes an electrostatic agent; and
a suspension including:
a liquid carrier; and
a plurality of functionalized plasmonic nanostructures dispersed throughout the liquid carrier, wherein each of the functionalized plasmonic nanostructures includes:
a plasmonic nanostructure core;
a polymeric hydrogel attached to the plasmonic nanostructure core, the polymeric hydrogel having a thickness ranging from about 10 nm to about 200 nm;
a plurality of two primers that together seed and amplify a template nucleic acid strand, the plurality of two primers being attached to side chains or arms of the polymeric hydrogel, wherein at least some of the plurality of primers are attached to the polymeric hydrogel at different distances from the plasmonic nanostructure core; and
a mechanism to attach to the capture site of the flow cell.

10. The kit as defined in claim 9, wherein the plasmonic nanostructure core is selected from the group consisting of a gold nanostructure, a silver nanostructure, a tin nanostructure, a rhodium nanostructure, a ruthenium nanostructure, a palladium nanostructure, an osmium nanostructure, an iridium nanostructure, a platinum nanostructure, a chromium nanostructure, a copper nanostructure, a gallium arsenide nanostructure, a doped silicon nanostructure, an aluminum nanostructure, a magnesium nanostructure, a silver and gold composite nanostructure, and combinations thereof.

11. The kit as defined in claim 9, wherein:
the polymeric hydrogel includes at least one acrylamide monomer unit; and
the polymeric hydrogel is a linear polymeric hydrogel or a branched polymeric hydrogel.

12. The kit as defined in claim 9, wherein:
each of the plurality of capture sites is the magnetic capture site; and
the mechanism is a magnetic material included in the plasmonic nanostructure core.

13. The kit as defined in claim 9, wherein:
each of the plurality of capture sites includes the chemical capture agent;
the mechanism is a functional agent incorporated into the polymeric hydrogel; and
one of:
the chemical capture agent is a capture oligonucleotide and the mechanism is a target nucleic acid that is complementary to the capture oligonucleotide; or
the mechanism is a member of a binding pair and the chemical capture agent is a second member of the binding pair.

14. The kit as defined in claim 9, wherein:
each of the plurality of capture sites includes the electrostatic capture agent; and
the mechanism is a reversibly chargeable functional group attached to the polymeric hydrogel.

15. The kit as defined in claim 9, wherein the different distances range from greater than 0 nm to about 20 nm.

16. The kit as defined in claim 9, wherein:
the flow cell further includes a substrate that supports the plurality of capture sites;
the substrate includes depressions separated by interstitial regions; and
at least one of the plurality of capture sites is positioned in each of the depressions.

17. The kit as defined in claim 9, wherein:
the flow cell further includes a substrate that supports the plurality of capture sites;
the substrate includes posts separated by interstitial regions; and
at least one of the plurality of capture sites is positioned over each of the posts.

18. The kit as defined in claim 9, wherein:
the flow cell further includes a substrate that supports the plurality of capture sites;
the substrate has a substantially flat surface; and
the plurality of capture sites is positioned in a pattern across the substantially flat surface.

19. A flow cell, comprising:
a substrate including a plurality of capture sites, wherein each capture site is a magnetic capture site, or includes a chemical capture agent, or includes an electrostatic agent; and
functionalized plasmonic nanostructures anchored to at least some of the plurality of capture sites, each functionalized plasmonic nanostructure including:
a plasmonic nanostructure core;
a polymeric hydrogel attached to the plasmonic nanostructure core, the polymeric hydrogel having a thickness ranging from about 10 nm to about 200 nm;
a plurality of two primers that together seed and amplify a template nucleic acid strand, the plurality of two primers being attached to side chains or arms of the polymeric hydrogel, wherein at least some of the plurality of primers are attached to the polymeric hydrogel at different distances from the plasmonic nanostructure core; and
a mechanism anchoring the functionalized plasmonic nanostructure to the capture site.

20. The flow cell as defined in claim 19, wherein:
each of the plurality of capture sites is the magnetic capture site; and
the mechanism is a magnetic material included in the plasmonic nanostructure core.

21. The flow cell as defined in claim 19, wherein:
each of the plurality of capture sites includes the chemical capture agent; and
the mechanism is a functional agent incorporated the polymeric hydrogel.

22. The flow cell as defined in claim 19, wherein the different distances range from greater than 0 nm to about 20 nm.

23. The flow cell as defined in claim 19, wherein:
the substrate includes depressions separated by interstitial regions; and
at least one of the plurality of capture sites is positioned in each of the depressions.

24. The flow cell as defined in claim 19, wherein:
the substrate includes posts separated by interstitial regions; and
at least one of the plurality of capture sites is positioned over each of the posts.

25. The flow cell as defined in claim 19, wherein:
the substrate has a substantially flat surface; and
the plurality of capture sites is positioned in a pattern across the substantially flat surface.

26. A method, comprising:
preparing a plurality of functionalized plasmonic nanostructures, wherein each of the functionalized plasmonic nanostructures includes:
a plasmonic nanostructure core;
a polymeric hydrogel attached to the plasmonic nanostructure core, the polymeric hydrogel having a thickness ranging from about 10 nm to about 200 nm;
a plurality of two primers that together seed and amplify a template nucleic acid strand, the plurality of two primers being attached to side chains of the polymeric hydrogel, wherein at least some of the plurality of primers are attached to the polymeric hydrogel at different distances from the plasmonic nanostructure core; and
a mechanism to anchor each of the functionalized plasmonic nanostructures to capture sites of a flow cell; and
dispersing the functionalized plasmonic nanostructures throughout a liquid carrier.

27. The method as defined in claim 26, wherein preparing the functionalized plasmonic nanostructures involves:
copolymerizing monomers to form the polymeric hydrogel;
grafting the plurality of two primers to the polymeric hydrogel to generate a pre-grafted polymeric hydrogel; and
coating the pre-grafted polymeric hydrogel on the plasmonic nanostructure core.

28. The method as defined in claim 27, further comprising incorporating the mechanism after the polymeric hydrogel is formed.

29. The method as defined in claim 26, wherein preparing the functionalized plasmonic nanostructures involves:
copolymerizing a first monomer and a second monomer in the presence of the plasmonic nanostructure core to form the polymeric hydrogel, the first monomer having a first functional group to attach to the primer and the second monomer having a second functional group to attach to an anchoring surface group on the plasmonic nanostructure core;
quenching polymerization when the thickness is achieved; and
grafting the plurality of two primers to the polymeric hydrogel.

30. The method as defined in claim 29, further comprising incorporating the mechanism after the polymeric hydrogel is formed.

31. A method, comprising:
introducing a template nucleic acid strand to a plasmonic enhancing suspension, the plasmonic enhancing suspension including:
a liquid carrier; and
a plurality of functionalized plasmonic nanostructures dispersed throughout the liquid carrier, wherein each of the functionalized plasmonic nanostructures includes:
a plasmonic nanostructure core;
a polymeric hydrogel attached to the plasmonic nanostructure core, the polymeric hydrogel having a thickness ranging from about 10 nm to about 200 nm;
a plurality of two primers that together seed and amplify the template nucleic acid strand, the plurality of two primers being attached to side chains or arms of the polymeric hydrogel, wherein at least some of the plurality of primers are attached to the polymeric hydrogel at different distances from the plasmonic nanostructure core; and
a mechanism to anchor each of the functionalized plasmonic nanostructures to capture sites of a flow cell;
initiating amplification of the template nucleic acid strand on the functionalized plasmonic nanostructures to form functionalized plasmonic nanostructures with a cluster of the template nucleic acid strands; and
introducing the functionalized plasmonic nanostructures with the cluster of the template nucleic acid strands into a flow cell including a plurality of the capture sites, whereby at least some of the functionalized plasmonic nanostructures respectively attach to at least some of the capture sites.

* * * * *